US012644156B2

(12) United States Patent
Maiuri et al.

(10) Patent No.: US 12,644,156 B2

(45) Date of Patent: Jun. 2, 2026

(54) METHODS FOR DIAGNOSING, PROGNOSING AND MANAGING TREATMENT OF BREAST CANCER

(71) Applicants: INSERM (Institut National de la Santé et de la Recherche Médicale), Paris (FR); Ceinge Biotecnologie Avanzate SCARL, Naples (IT); Institut Gustave Roussy, Villejuif (FR); Sorbonne Université, Paris (FR); Université Paris Cité, Paris (FR); Assistance Publique-Hôpitaux de Paris (APHP), Paris (FR)

(72) Inventors: Maria Chiara Maiuri, Paris Cedex (FR); Guido Kroemer, Paris Cedex (FR); Jonathan Pol, Paris Cedex (FR); Francesco Salvatore, Naples (IT); Fatima De Palma, Naples (IT); Valentina Del Monaco, Naples (IT)

(73) Assignees: INSTIT NATIONAL DE LA SANTE ET DE AL RECHERCHE MEDICALE (INSERM), Paris (FR); Ceinge Biotecnologie Avanzate SCARL, Naples (IT); Institut Gustave Roussy, Villejuif (FR); Sorbonne Université, Paris (FR); Université Paris Cité, Paris (FR); Assistance Publique-Hôpitaux de Paris (APHP), Paris (FR)

( * ) Notice: Subject to any disclaimer, the term of this patent is extended or adjusted under 35 U.S.C. 154(b) by 829 days.

(21) Appl. No.: 17/904,910

(22) PCT Filed: Feb. 26, 2021

(86) PCT No.: PCT/EP2021/054785

§ 371 (c)(1),
(2) Date: Aug. 24, 2022

(87) PCT Pub. No.: WO2021/170777

PCT Pub. Date: Sep. 2, 2021

(65) Prior Publication Data

US 2023/0113705 A1 Apr. 13, 2023

(30) Foreign Application Priority Data

Feb. 28, 2020 (EP) .................................... 20305211

(51) Int. Cl.
*C12Q 1/68* (2018.01)
*C12Q 1/6886* (2018.01)

(52) U.S. Cl.
CPC ...... *C12Q 1/6886* (2013.01); *C12Q 2600/118* (2013.01); *C12Q 2600/158* (2013.01); *C12Q 2600/178* (2013.01)

(58) Field of Classification Search
None
See application file for complete search history.

(56) References Cited

PUBLICATIONS

Salvador (Cancer Res (2020) 80 (4_Supplement): P1-05-09) (Year: 2020).*

Yang et al. (Gene 591(2016) 471-477) (Year: 2016).*

Caparica et al. (ESMO Open 2019;4:e000504. doi:10.1136/esmoopen-2019-000504). (Year: 2019).*

Tripathy et al.; "Unravelling the role of long non-coding RNA-LINC01087 in breast cancer"; Non-Coding RNA Research, vol. 5, No. 1, Dec. 24, 2019, pp. 1-10.

Yang et al.; "Co-expression networks revealed potential core IncRNAs in the triple-negative breast cancer"; Gene, vol. 591, No. 2, Jul. 2, 2016, pp. 471-477.

Naorem et al.; "Comprehensive analysis of dysregulated IncRNAs and their competing endogenous RNA network in triple-negative breast cancer"; International Journal of Biological Macromolecules, vol. 145, Dec. 26, 2019.

* cited by examiner

*Primary Examiner* — Juliet C Switzer

(74) *Attorney, Agent, or Firm* — WCF IP

(57) ABSTRACT

The present invention relates to methods and compositions for the care of breast cancer, from diagnosis to treatment management. The inventors show that LINC01087 down-regulation contributes to a more aggressive phenotype of BC, and could represents a novel and promising specific biomarker for the diagnosis of triple-negative breast cancer. The inventors show that LINC01087 upregulation contributes to a less aggressive phenotype of BC, and could represents a novel and promising specific biomarker for the diagnosis of luminal BCs. The invention relates to a method comprising the steps of: i) determining the expression level of the long intergenic non-coding RNA 01087 (LINC01087) in a sample obtained from the subject, and ii) comparing the expression level determined at step i) with a predetermined reference value, wherein detecting difference between the expression level determined at step i) and the predetermined reference value is indicative of an aggressive TNBC or less aggressive luminal BCs.

2 Claims, 8 Drawing Sheets

METHODS FOR DIAGNOSING, PROGNOSING AND MANAGING TREATMENT OF BREAST CANCER

FIELD OF THE INVENTION

Figures 1A, 1B:
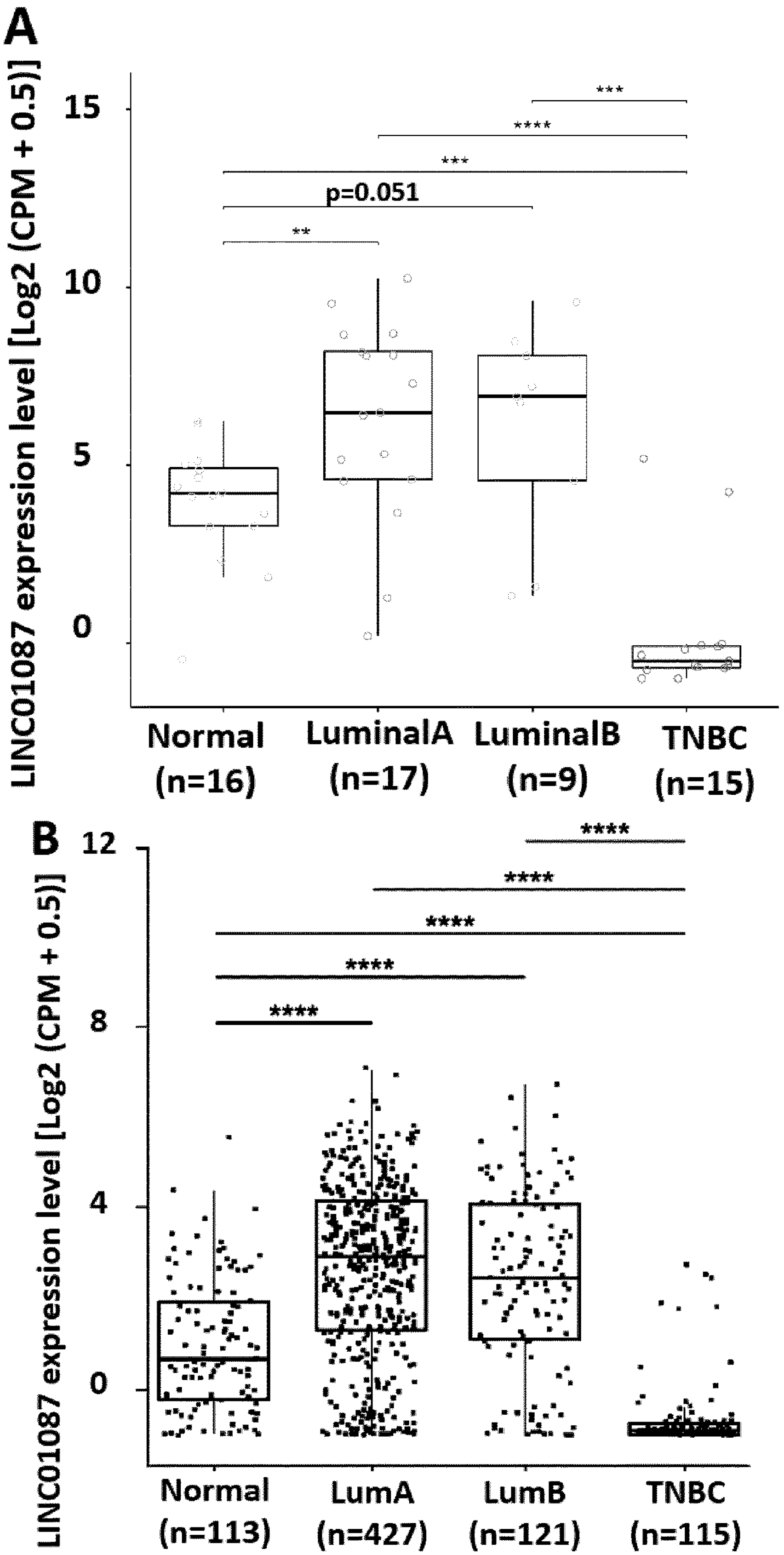

The invention is in the field of oncology, more particularly the invention relates to methods and compositions for the diagnosis, prognosis and the treatment management of breast cancer. The present invention also relates to the use of the long intergenic non-coding RNA 01087 (LINC01087) as a biomarker of breast cancer.

BACKGROUND OF THE INVENTION

Breast cancer (BC) is a heterogeneous group of diseases, each one characterized by different biological and clinical features[1]. Based on the expression of the receptors of progesterone (PR) and oestrogen (ER) and of Erb-B2 receptor tyrosine kinase 2 (ERBB2, best known as the human epidermal growth factor receptor 2, HER2), BCs have been subclassified into five molecular subtypes: Luminal A, Luminal B, HER2 positive (HER2+), Normal-like, and triple-negative breast cancer (TNBC)[2,3]. Among them, TNBC refers to a collection of tumors with different clinical, histological and molecular imprints. TNBC is clinically defined by the lack of ER, PR and HER2 receptors, which are the molecular targets of the current immunotherapies (i.e. pertuzumab, trastuzumab) and targeted chemotherapies (i.e. lapatinib) of the other three types of BC.[4-6] TNBC is an aggressive subtype, exhibiting high risk of recurrence during the three-year period after diagnosis and of distant metastasis, low survival and the poorest prognosis compared to the other BC subsets[7,8].

Advancements in the 'omics' technologies have provided remarkable progresses in understanding the molecular heterogeneity within and between BC tumors, identifying promising genetic and epigenetic BC-specific biomarkers[9-12]. In fact, BC molecular signatures, in association with the canonical histological tests, not only strengthened disease detection, prevention, and then management, but also became crucial to better decide the appropriate treatment according to the tumor subtype.

On the basis of this concept, an increasing number of studies have explored the key role of long noncoding RNAs (lncRNAs) in human diseases, such as BC[13-16]. LncRNAs are non-protein-coding transcripts longer than 200 nucleotides in length. They are involved in a variety of mechanisms such as epigenetic, transcriptional and post-transcriptional regulation as well as chromatin remodelling[17]. LncRNAs can be classified into five categories: sense, antisense, bidirectional, intronic and intergenic, according to their position on the genome[18].

The involvement of lncRNAs in breast carcinogenesis, metastasis and chemotherapy resistance has been reported[19-21]. In addition, due to their dysregulated expression, lncRNAs have also been recognized as promising subtype-specific biomarkers for early detection of BC and disease monitoring[13,20,22-27].

The inventors have investigated the functional and clinical role of the long intergenic non-coding RNA 01087 (LINC01087) in breast cancer. They assessed: i) LINC01087 expression in different human BC subtypes and cell lines; ii) the potential role of LINC01087 as an indicator of patient's clinical outcome in luminal A and B breast cancers; iii) the potential role of LINC01087 as an indicator of patient's clinical outcome in TNBC; iv) LINC01087 expression in different histological BC types; v) the association between the variations in LINC01087 expression and the mutational status of TP53 and BRCA1/2; vi) the effects of LINC01087 knockdown on cell proliferation and cell cycle. Theirs findings provide evidence that LINC01087 dysregulation may contribute to BC. They can speculate that the involvement of LINC01087 in breast oncogenesis could be related to its direct participation in cell proliferation and survival.

There is still a need for biomarker of BC subtypes. Here, the inventors present the evidence that aberrant expression of LINC01087 could be used in the clinical practise as a novel highly specific diagnostic biomarker for distinguishing BC luminal and TNBC molecular subtypes, and as a bad prognostic biomarker for TNBC patients as well as a good prognostic biomarker for luminal patients.

SUMMARY OF THE INVENTION

The invention is in the field of oncology, more particularly the invention relates to methods and compositions for the diagnosis, the prognosis and the treatment management of breast cancer. The present invention relates to use of the long intergenic non-coding RNA 01087 (LINC01087) as a biomarker of breast cancer (BC). In particular, the present invention is defined by the claims.

DETAILED DESCRIPTION OF THE INVENTION

Long non-coding RNAs (lncRNAs) are a group of transcripts that do not exhibit a protein-coding potential. Emerging studies revealed that they play a regulatory role in several human diseases, including cancer. Breast cancer (BC) is a leading cause of death worldwide. Compared to the other BC subsets, the triple-negative breast cancer (TNBC) subtype presents an aggressive clinical behaviour and is associated with poor prognosis and low survival rate, while luminal BCs, particularly luminal A, are associated with better prognosis and survival rate. In this scenario, lncRNAs are emerging as contributors of breast carcinogenesis and promising biomarkers for BC diagnosis and prognosis evaluation. Hence, in this study, the inventors have identified the long intergenic non-coding RNA 01087 (LINC01087) as a relevant participant in breast oncogenesis. The inventors found that LINC01087 was differentially expressed in the heterogeneous population of BC subtypes, being significantly downregulated in TNBCs, and upregulated in the luminal subtypes. Thus, they explored the prognostic role of LINC01087 in TNBC and luminal subtypes in silico, by analysing survival curves in the Kaplan-Meier plotter online database. They also assessed if LINC01087 dysregulation could be implicated in the aggressiveness of BC by associating its expression with the mutational status of the genes TP53 and BRCA1/2. As a result, LINC01087 down-expression was significantly associated with a worse relapse-free survival in TNBC patients. Moreover, BC patients harbouring alterations in TP53 gene presented LINC01087 strongly downregulated when compared to TP53 wild-type patients; a correlation that resulted from a dominance of the TNBC subtype in TP53-mutated tumors. Moreover, BC patients harbouring alterations in BRCA1 gene presented LINC01087 strongly downregulated when compared to BRCA1 wild-type patients; a correlation that resulted from a dominance of the TNBC subtype in BRCA1-mutated tumors. Additionally, LINC01087 over-expression was significantly associated with a better relapse-free survival in luminal patients. Among patients bearing TP53 mutated BCs, LINC01087 was strongly upregulated when compared to TNBC patients.

Finally, functional analysis revealed that LINC01087 knockdown impacts cell cycle and increases cell proliferation.

Altogether, these data strongly suggest that LINC01087 is a promising biomarker to distinguish TNBC and luminal BC subtypes. Precisely, LINC01087 downregulation contributes to a more aggressive phenotype of BC, and could represent a novel and specific biomarker not only for the diagnosis of TNBC, but also to predict a worse clinical outcome. In contrast, LINC01087 upregulation would contribute to a less aggressive phenotype of BC, and could represent a novel and promising specific biomarker not only for the diagnosis of luminal subtypes, but also to predict a better clinical outcome.

Method for Diagnosing Breast Cancer

Accordingly, the first object of the present invention relates to a method of determining whether a subject has or is at a risk of developing a breast cancer (BC) comprising the steps of: i) determining the expression level of the long intergenic non-coding RNA 01087 (LINC01087) in a sample obtained from the subject, and ii) comparing the expression level determined at step i) with a predetermined reference value wherein detecting difference between the expression level determined at step i) and the predetermined reference value is indicative of whether a subject has or is at a risk of developing a breast cancer.

As used herein, the term "subject" denotes a mammal, such as a rodent, a feline, a canine, and a primate. Particularly, the subject according to the invention is a human. As used herein, the term "subject" encompasses "patient".

In one embodiment, the subject has or is at a risk of having cancer.

The terms "cancer" has its general meaning in the art and refers to a group of diseases involving abnormal cell growth with the potential to invade or spread to other parts of the body. The term "cancer" further encompasses both primary and metastatic cancers.

In one embodiment, the subject has or is at a risk of having breast cancer.

As used herein, the term "breast cancer" refers to any neoplastic pathology of the breast tissue, and includes all histological and molecular subtypes of breast neoplasia.

The term "breast cancer tumor" designates the abnormal mass of breast tissue composed of cancer, malignant cells. The American Joint Committee on Cancer (AJCC) provides two principal groups for breast cancer staging: anatomic, which is based on extent of cancer as defined by tumor size (T), lymph node status (N), and distant metastasis (M); and prognostic which includes anatomic TNM plus tumor grade and the status of the biomarkers human epidermal growth factor receptor 2 (HER2), estrogen receptor (ER), and progesterone receptor (PR). (Kalli S., Semine A., Cohen S., Naber S. P., Makim S. S., BahlAmerican M. Joint Committee on Cancer's Staging System for Breast Cancer, Eighth Edition: What the Radiologist Needs to Know. Radiographics. 2018 November-December; 38(7):1921-1933).

The first group called "anatomic" is divided in different stages:

- Stage 0: non-invasive cancer
- Stage 1, patients usually have invasive breast cancer, while 1A refers to a tumor smaller than two centimeters that has spread to the lymph nodes but not outside the breasts, and 1B can mean: no cancer is seen in the breast, but a few cancer cells are found in the lymph nodes under the arm (known as micrometastasis) or the cancer in the breast is 2 cm or smaller and a few cancer cells are found in the lymph nodes under the arm (micrometastasis).
- Stage 2A is when no cancer is seen in the breast but cancer is found in one to three lymph nodes under the arm or near the breastbone or the cancer in the breast is 2 cm or smaller and cancer is found in one to three lymph nodes under the arm or near the breastbone or the cancer in the breast is larger than 2 cm but smaller than 5 cm and no cancer is found in the lymph nodes under the arm. Stage 2B can mean the cancer in the breast is larger than 2 cm but smaller than 5 cm. Cancer is found in one to three lymph nodes under the arm or near the breastbone or the cancer in the breast is larger than 5 cm and no cancer is found in the lymph nodes under the arm.
- Stage 3 describes a more aggressive form of invasive breast cancer and is divided into three sub phases (3A, 3B and 3C). Stage 3A can mean No cancer is seen in the breast, but cancer is found in four to nine lymph nodes under the arm or near the breastbone or the cancer in the breast measures up to 5 cm and cancer is found in four to nine lymph nodes under the arm or near the breastbone or the cancer in the breast is larger than 5 cm, and cancer is found in up to three lymph nodes under the arm or near the breastbone. Stage 3B means the cancer in the breast can be any size and has spread to the skin of the breast or chest wall. Cancer is found in up to nine lymph nodes under the arm or near the breast bone. Stage 3C means the cancer in the breast can be any size, may have spread to the skin of the breast or chest wall and cancer is found in 10 or more lymph nodes under the arm or near the breastbone, or to nodes above or below the collarbone.
- Stage 4 indicates that the cancer has spread to other organs of the body (called distant metastasis) such as the lungs, the liver, distant lymph nodes, skin, or bones.

The second group "prognostic" corresponds to molecular subtypes of breast cancer that are based on the genes a cancer expresses:

- Luminal A breast cancer (luminal BC subtype) is hormone-receptor positive (estrogen-receptor and/or progesterone-receptor positive), HER2 negative, and has low levels of the protein Ki-67, which helps control how fast cancer cells grow. Luminal A cancers are low-grade, tend to grow slowly and have the best prognosis.
- Luminal B breast cancer (luminal BC subtype) is hormone-receptor positive (estrogen-receptor and/or progesterone-receptor positive), and either HER2 positive or HER2 negative with high levels of Ki-67. Luminal B cancers generally grow slightly faster than luminal A cancers and their prognosis is slightly worse.
- HER2-enriched breast cancer is hormone-receptor negative (estrogen-receptor and progesterone-receptor negative) and HER2 positive. HER2-enriched cancers tend to grow faster than luminal cancers and can have a worse prognosis, but they are often successfully treated with targeted therapies aimed at the HER2 protein, such as Herceptin (chemical name: trastuzumab), Perjeta (chemical name: pertuzumab), Tykerb (chemical name: lapatinib), Nerlynx (chemical name: neratinib), and Kadcyla (chemical name: T-DM1 or ado-trastuzumab emtansine).

Normal-like breast cancer is similar to luminal A disease: hormone-receptor positive (estrogen-receptor and/or progesterone-receptor positive), HER2 negative, and has low levels of the protein Ki-67, which helps control how fast cancer cells grow. Still, while normal-like breast cancer has a good prognosis, its prognosis is slightly worse than luminal A cancer's prognosis.

Triple-negative/basal-like breast cancer (TNBC) is hormone-receptor negative (estrogen-receptor and progesterone-receptor negative) and HER2 negative. This type of cancer is more common in women with BRCA1 gene mutations.

In one embodiment, the subject has or is at a risk of having triple-negative breast cancer (TNBC).

In one embodiment, the subject has or is at a risk of having luminal BC subtypes. In particular, the subject has or is at a risk of having Luminal A breast cancer. In particular, the subject has or is at a risk of having Luminal B breast cancer.

The inventors show that the LINC01087 downregulation is associated with a more aggressive phenotype of TNBC and a poor relapse-free survival in TNBC patients. Typically, the term "downregulation" indicates that the expression level of LINC01087 is significantly lower than the expression level of the same gene in the healthy breast tissue.

In one embodiment, the present invention relates to a method of determining whether a subject has or is at a risk of developing a triple-negative breast cancer (TNBC) comprising the steps of: i) determining the expression level of the long intergenic non-coding RNA 01087 (LINC01087) in a sample obtained from the subject, and ii) comparing the expression level determined at step i) with a predetermined reference value wherein detecting difference between the expression level determined at step i) and the predetermined reference value is indicative of whether a subject has or is at a risk of developing a TNBC.

In one embodiment, the present invention relates to a method of determining whether a subject has or is at a risk of developing a TNBC comprising the steps of: i) determining the expression level of the long intergenic non-coding RNA 01087 (LINC01087) in a sample obtained from the subject, and ii) comparing the expression level determined at step i) with a predetermined reference value and wherein when the expression level of the LINC01087 is lower than the predetermined reference value, it is considered that the subject has or is at a risk of having TNBC.

In some embodiment, when the expression level of the LINC01087 is lower than the predetermined reference value, it is considered that the subject has or is at a risk of having triple-negative breast cancer (TNBC).

The inventors show that the LINC01087 upregulation is associated with a luminal breast cancer (BC) subtype. The LINC01087 upregulation is associated with a less aggressive phenotype of luminal BC subtypes and with a better relapse-free survival in luminal BC patients. Typically, the term "upregulation" indicates that the expression level of LINC01087 is significantly higher than the expression level of the same gene in the healthy breast tissue.

In one embodiment, the present invention relates to a method of determining whether a subject has or is at a risk of developing luminal BC subtypes comprising the steps of: i) determining the expression level of the long intergenic non-coding RNA 01087 (LINC01087) in a sample obtained from the subject, and ii) comparing the expression level determined at step i) with a predetermined reference value wherein detecting difference between the expression level determined at step i) and the predetermined reference value is indicative of whether a subject has or is at a risk of developing luminal BC subtypes.

In one embodiment, the present invention relates to a method of determining whether a subject has or is at a risk of developing luminal BC subtypes comprising the steps of: i) determining the expression level of the long intergenic non-coding RNA 01087 (LINC01087) in a sample obtained from the subject, and ii) comparing the expression level determined at step i) with a predetermined reference value and iii) wherein when the expression level of the LINC01087 is higher than the predetermined reference value, it is considered that the subject has or is at a risk of having luminal BC subtypes.

In some embodiment, when the expression level of the LINC01087 is higher than the predetermined reference value, it is considered that the subject has or is at a risk of having a luminal BC subtypes.

Depending on the type of cancers (e.g. TNBC or luminal BC subtypes), the predetermined reference value may change or may be the same.

The person skilled in the art knows how to determine a predetermined reference value and the predetermined reference value are determined by the same way.

As used herein, the term "sample" refers to any sample obtained from a subject, such as a serum sample, a plasma sample, a urine sample, a blood sample, a lymph sample, or a tissue biopsy. In a particular embodiment, the sample is a tissue biopsy.

As used herein, the term "tissue", when used in reference to a part of a body or of an organ, generally refers to an aggregation or collection of morphologically similar cells and associated accessory and support cells and intercellular matter, including extracellular matrix material, vascular supply, and fluids, acting together to perform specific functions in the body. There are generally four basic types of tissue in animals and humans including muscle, nerve, epithelial, and connective tissues.

In some embodiments, when the subject suffers from a cancer, the tissue sample is a tumor tissue sample. As used herein, the term "tumor tissue sample" means any tissue tumor sample derived from the subject. Said tissue sample is obtained for the purpose of the in vitro evaluation. In some embodiments, the tumor sample may result from the tumor resected from the subject. In some embodiments, the tumor sample may result from a biopsy performed in the primary tumour of the subject or performed in metastatic sample distant from the primary tumor of the subject. In some embodiments, the tumor tissue sample encompasses a global primary tumor (as a whole), a tissue sample from the center of the tumor, a tumor tissue sample collected prior surgery (for follow-up of subjects after treatment for example), and a distant metastasis. The tumor tissue sample can, of course, be subjected to a variety of well-known post-collection preparative and storage techniques (e.g., fixation, storage, freezing, etc.). The sample can be fresh, frozen, fixed (e.g., formalin fixed), or embedded (e.g., paraffin embedded).

As used herein, the term "control sample" refers to a breast tissue or cells from a healthy subject, or to a healthy tissue of the subject. The control sample may also refer to:

i. a positive control sample indicative of the amount and/or expression level of said lncRNA transcript in a subject suffering from breast cancer with poor prognosis;

ii. a negative control sample indicative of the amount and/or expression level of said lncRNA transcript in a healthy individual or in a healthy tissue of the subject.

As used herein, the term “risk” in the context of the present invention, relates to the probability that an event will occur over a specific time period and can mean a subject’s “absolute” risk or “relative” risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula p/(l−p) where p is the probability of event and (l−p) is the probability of no event) to no-conversion. “Risk evaluation,” or “evaluation of risk” in the context of the present invention encompasses making a prediction of the probability, odds, or likelihood that an event or disease state may occur, the rate of occurrence of the event or conversion from one disease state to another. Risk evaluation can also comprise prediction of future clinical parameters, traditional laboratory risk factor values, or other indices of relapse, either in absolute or relative terms in reference to a previously measured population. The methods of the present invention may be used to make continuous or categorical measurements of the risk of conversion, thus diagnosing and defining the risk spectrum of a category of subjects defined as being at risk of conversion. In the categorical scenario, the invention can be used to discriminate between normal and other subject cohorts at higher risk. In some embodiments, the present invention may be used so as to discriminate those at risk from normal.

Thus the expression “determining whether a patient is at risk of having a breast cancer” as used herein means that the patient to be analyzed by the method of the present invention is allocated either into the group of patients of a population having an elevated risk, or into a group having a reduced risk of having breast cancer. An elevated risk as referred to in accordance with the present invention, preferably, means that the risk of having breast cancer within a predetermined predictive window is elevated significantly (i.e. increased significantly) for a patient with respect to the average risk measured in a general population. A reduced risk as referred to in accordance with the present invention, preferably, means that the risk of having breast cancer within a predetermined predictive window is reduced significantly for a patient with respect to the average risk measured in the general population. Particularly, a significant increase or reduction of a risk is an increase or reduction or a risk of a size which is considered to be significant for prognosis, particularly said increase or reduction is considered statistically significant. The terms “significant” and “statistically significant” are known by the person skilled in the art. Thus, whether an increase or reduction of a risk is significant or statistically significant can be determined without further ado by the person skilled in the art using various well known statistic evaluation tools.

As used herein the term “long intergenic non-coding RNA” has its general meaning in the art and refers to an a type of RNA, defined as being transcripts with lengths exceeding 200 nucleotides that are not translated into protein.

As used herein the term “long intergenic non-coding RNA 01087” (LINC01087) has its general meaning in the art and refers to an intergenic long intergenic non-coding RNA (lncRNA) spanning 3516 bp on the 2q21.1 chromosome. It is composed of two exons and is expressed in human normal tissues of breast and testis. The naturally occurring human LINC01087 gene has a nucleotide sequence having the following number: Gene ID: 101927994 (NCBI reference).

In some embodiments, the expression level of the lncRNA transcript is determined at nucleic acid level. Typically, the measure may be carried out directly on an extracted messenger RNA (mRNA) sample, or on retrotranscribed complementary DNA (cDNA) prepared from extracted mRNA by technologies well-known in the art. Typically, the level of lncRNA transcript is determined by determining the quantity of mRNA. For example the nucleic acid contained in the samples (e.g., cell or tissue prepared from the subject) is first extracted according to standard methods, for example using lytic enzymes or chemical solutions or extracted by nucleic-acid-binding resins following the manufacturer’s instructions. The extracted mRNA is then detected by hybridization (e. g., Northern blot analysis, in situ hybridization) and/or amplification (e.g., RT-PCR). Other methods of Amplification include ligase chain reaction (LCR), transcription-mediated amplification (TMA), strand displacement amplification (SDA) and nucleic acid sequence based amplification (NASBA).

Nucleic acids having at least 10 nucleotides and exhibiting sequence complementarity or homology to the mRNA of interest herein find utility as hybridization probes or amplification primers. It is understood that such nucleic acids need not be identical, but are typically at least about 80% identical to the homologous region of comparable size, more preferably 85% identical and even more preferably 90-95% identical. In some embodiments, it will be advantageous to use nucleic acids in combination with appropriate means, such as a detectable label, for detecting hybridization.

Typically, the nucleic acid probes include one or more labels, for example to permit detection of a target nucleic acid molecule using the disclosed probes. In various applications, such as in situ hybridization procedures, a nucleic acid probe includes a label (e.g., a detectable label). A “detectable label” is a molecule or material that can be used to produce a detectable signal that indicates the presence or concentration of the probe (particularly the bound or hybridized probe) in a sample. Thus, a labeled nucleic acid molecule provides an indicator of the presence or concentration of a target nucleic acid sequence (e.g., genomic target nucleic acid sequence) (to which the labeled uniquely specific nucleic acid molecule is bound or hybridized) in a sample. A label associated with one or more nucleic acid molecules (such as a probe generated by the disclosed methods) can be detected either directly or indirectly. A label can be detected by any known or yet to be discovered mechanism including absorption, emission and/or scattering of a photon (including radio frequency, microwave frequency, infrared frequency, visible frequency and ultra-violet frequency photons). Detectable labels include colored, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens that can be detected by antibody binding interactions, and paramagnetic and magnetic molecules or materials.

Particular examples of detectable labels include fluorescent molecules (or fluorochromes). Numerous fluorochromes are known to those of skill in the art, and can be selected, for example from Life Technologies (formerly Invitrogen), e.g., see, The Handbook—A Guide to Fluorescent Probes and Labeling Technologies). Examples of particular fluorophores that can be attached (for example, chemically conjugated) to a nucleic acid molecule (such as a uniquely specific binding region) are provided in U.S. Pat. No. 5,866,366 to Nazarenko et al., such as 4-acetamido-4'-isothiocyanatostilbene-2,2' disulfonic acid, acridine and derivatives such as acridine and acridine isothiocyanate, 5-(2'-aminoethyl) aminonaphthalene-1-sulfonic acid (EDANS), 4-amino-N-[3 vinylsulfonyl)phenyl]naphthalimide-3,5 disulfonate (Lucifer Yellow VS), N-(4-anilino-1-naphthyl)maleimide, antl1ranilamide, Brilliant Yellow, coumarin and derivatives such as coumarin, 7-amino-4-methylcoumarin (AMC, Coumarin 120), 7-amino-4-trifluoromethylcouluarin (Coumarin 151); cyanosine; 4',6-diarninidino-2-phenylindole (DAPI); 5',5"dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulforlic acid; 5-[dimethylamino] naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4, 6dicl1lorotriazin-2-yDarninofluorescein (DTAF), 2'7'dimethoxy-4'5'-dichloro-6-carboxyfluorescein (JOE), fluorescein, fluorescein isothiocyanate (FITC), and QFITC Q(RITC); 2',7'-difluorofluorescein (OREGON GREEN®); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, rhodamine green, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives. Other suitable fluorophores include thiol-reactive europium chelates which emit at approximately 617 mn (Heyduk and Heyduk, Analyt. Biochem. 248:216-27, 1997; J. Biol. Chem. 274:3315-22, 1999), as well as GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al.) and derivatives thereof. Other fluorophores known to those skilled in the art can also be used, for example those available from Life Technologies (Invitrogen; Molecular Probes (Eugene, Oreg.)) and including the ALEXA FLUOR® series of dyes (for example, as described in U.S. Pat. Nos. 5,696,157, 6, 130, 101 and 6,716,979), the BODIPY series of dyes (dipyrrometheneboron difluoride dyes, for example as described in U.S. Pat. Nos. 4,774,339, 5,187,288, 5,248,782, 5,274,113, 5,338, 854, 5,451,663 and 5,433,896), Cascade Blue (an amine reactive derivative of the sulfonated pyrene described in U.S. Pat. No. 5,132,432) and Marina Blue (U.S. Pat. No. 5,830,912).

In addition to the fluorochromes described above, a fluorescent label can be a fluorescent nanoparticle, such as a semiconductor nanocrystal, e.g., a QUANTUM DOT™ (obtained, for example, from Life Technologies (QuantumDot Corp, Invitrogen Nanocrystal Technologies, Eugene, Oreg.); see also, U.S. Pat. Nos. 6,815,064; 6,682,596; and 6,649,138). Semiconductor nanocrystals are microscopic particles having size-dependent optical and/or electrical properties. When semiconductor nanocrystals are illuminated with a primary energy source, a secondary emission of energy occurs of a frequency that corresponds to the handgap of the semiconductor material used in the semiconductor nanocrystal. This emission can be detected as colored light of a specific wavelength or fluorescence. Semiconductor nanocrystals with different spectral characteristics are described in e.g., U.S. Pat. No. 6,602,671. Semiconductor nanocrystals that can be coupled to a variety of biological molecules (including dNTPs and/or nucleic acids) or substrates by techniques described in, for example, Bruchez et al., Science 281:20132016, 1998; Chan et al., Science 281: 2016-2018, 1998; and U.S. Pat. No. 6,274,323. Formation of semiconductor nanocrystals of various compositions are disclosed in, e.g., U.S. Pat. Nos. 6,927,069; 6,914,256; 6,855,202; 6,709,929; 6,689,338; 6,500,622; 6,306,736; 6,225,198; 6,207,392; 6,114,038; 6,048,616; 5,990,479; 5,690,807; 5,571,018; 5,505,928; 5,262,357 and in U.S. Patent Publication No. 2003/0165951 as well as PCT Publication No. 99/26299 (published May 27, 1999). Separate populations of semiconductor nanocrystals can be produced that are identifiable based on their different spectral characteristics. For example, semiconductor nanocrystals can be produced that emit light of different colors based on their composition, size or size and composition. For example, quantum dots that emit light at different wavelengths based on size (565 mn, 655 mn, 705 mn, or 800 mn emission wavelengths), which are suitable as fluorescent labels in the probes disclosed herein are available from Life Technologies (Carlshad, Calif.).

Additional labels include, for example, radioisotopes (such as 3 H), metal chelates such as DOTA and DPTA chelates of radioactive or paramagnetic metal ions like Gd3+, and liposomes. Detectable labels that can be used with nucleic acid molecules also include enzymes, for example horseradish peroxidase, alkaline phosphatase, acid phosphatase, glucose oxidase, beta-galactosidase, beta-glucuronidase, or beta-lactamase. Alternatively, an enzyme can be used in a metallographic detection scheme. For example, silver in situ hyhridization (SISH) procedures involve metallographic detection schemes for identification and localization of a hybridized genomic target nucleic acid sequence. Metallographic detection methods include using an enzyme, such as alkaline phosphatase, in combination with a water-soluble metal ion and a redox-inactive substrate of the enzyme. The substrate is converted to a redox-active agent by the enzyme, and the redoxactive agent reduces the metal ion, causing it to form a detectable precipitate. (See, for example, U.S. Patent Application Publication No. 2005/0100976, PCT Publication No. 2005/003777 and U.S. Patent Application Publication No. 2004/0265922). Metallographic detection methods also include using an oxidoreductase enzyme (such as horseradish peroxidase) along with a water soluble metal ion, an oxidizing agent and a reducing agent, again to form a detectable precipitate. (See, for example, U.S. Pat. No. 6,670,113).

Probes made using the disclosed methods can be used for nucleic acid detection, such as ISH procedures (for example, fluorescence in situ hybridization (FISH), chromogenic in situ hybridization (CISH) and silver in situ hybridization (SISH)) or comparative genomic hybridization (CGH).

In situ hybridization (ISH) involves contacting a sample containing target nucleic acid sequence (e.g., genomic target nucleic acid sequence) in the context of a metaphase or interphase chromosome preparation (such as a cell or tissue sample mounted on a slide) with a labeled probe specifically hybridizable or specific for the target nucleic acid sequence (e.g., genomic target nucleic acid sequence). The slides are optionally pretreated, e.g., to remove paraffin or other materials that can interfere with uniform hybridization. The sample and the probe are both treated, for example by heating to denature the double stranded nucleic acids. The probe (formulated in a suitable hybridization buffer) and the sample are combined, under conditions and for sufficient time to permit hybridization to occur (typically to reach equilibrium). The chromosome preparation is washed to remove excess probe, and detection of specific labeling of the chromosome target is performed using standard techniques.

For example, a biotinylated probe can be detected using fluorescein-labeled avidin or avidin-alkaline phosphatase. For fluorochrome detection, the fluorochrome can be detected directly, or the samples can be incubated, for example, with fluorescein isothiocyanate (FITC)-conjugated avidin. Amplification of the FITC signal can be effected, if necessary, by incubation with biotin-conjugated goat antiavidin antibodies, washing and a second incubation with FITC-conjugated avidin. For detection by enzyme activity, samples can be incubated, for example, with streptavidin, washed, incubated with biotin-conjugated alkaline phosphatase, washed again and pre-equilibrated (e.g., in alkaline phosphatase (AP) buffer). For a general description of in situ hybridization procedures, see, e.g., U.S. Pat. No. 4,888,278.

Numerous procedures for FISH, CISH, and SISH are known in the art. For example, procedures for performing FISH are described in U.S. Pat. Nos. 5,447,841; 5,472,842; and 5,427,932; and for example, in Pirlkel et al., Proc. Natl. Acad. Sci. 83:2934-2938, 1986; Pinkel et al., Proc. Natl. Acad. Sci. 85:9138-9142, 1988; and Lichter et al., Proc. Natl. Acad. Sci. 85:9664-9668, 1988. CISH is described in, e.g., Tanner et al., Am. .l. Pathol. 157:1467-1472, 2000 and U.S. Pat. No. 6,942,970. Additional detection methods are provided in U.S. Pat. No. 6,280,929.

Numerous reagents and detection schemes can be employed in conjunction with FISH, CISH, and SISH procedures to improve sensitivity, resolution, or other desirable properties. As discussed above probes labeled with fluorophores (including fluorescent dyes and QUANTUM DOTS®) can be directly optically detected when performing FISH. Alternatively, the probe can be labeled with a nonfluorescent molecule, such as a hapten (such as the following non-limiting examples: biotin, digoxigenin, DNP, and various oxazoles, pyrrazoles, thiazoles, nitroaryls, benzofurazans, triterpenes, ureas, thioureas, rotenones, coumarin, courmarin-based compounds, Podophyllotoxin, Podophyllotoxin-based compounds, and combinations thereof), ligand or other indirectly detectable moiety. Probes labeled with such non-fluorescent molecules (and the target nucleic acid sequences to which they bind) can then be detected by contacting the sample (e.g., the cell or tissue sample to which the probe is bound) with a labeled detection reagent, such as an antibody (or receptor, or other specific binding partner) specific for the chosen hapten or ligand. The detection reagent can be labeled with a fluorophore (e.g., QUANTUM DOT®) or with another indirectly detectable moiety, or can be contacted with one or more additional specific binding agents (e.g., secondary or specific antibodies), which can be labeled with a fluorophore.

In other examples, the probe, or specific binding agent (such as an antibody, e.g., a primary antibody, receptor or other binding agent) is labeled with an enzyme that is capable of converting a fluorogenic or chromogenic composition into a detectable fluorescent, colored or otherwise detectable signal (e.g., as in deposition of detectable metal particles in SISH). As indicated above, the enzyme can be attached directly or indirectly via a linker to the relevant probe or detection reagent. Examples of suitable reagents (e.g., binding reagents) and chemistries (e.g., linker and attachment chemistries) are described in U.S. Patent Application Publication Nos. 2006/0246524; 2006/0246523, and 2007/01 17153.

It will be appreciated by those of skill in the art that by appropriately selecting labelled probe-specific binding agent pairs, multiplex detection schemes can be produced to facilitate detection of multiple target nucleic acid sequences (e.g., genomic target nucleic acid sequences) in a single assay (e.g., on a single cell or tissue sample or on more than one cell or tissue sample). For example, a first probe that corresponds to a first target sequence can be labelled with a first hapten, such as biotin, while a second probe that corresponds to a second target sequence can be labelled with a second hapten, such as DNP. Following exposure of the sample to the probes, the bound probes can be detected by contacting the sample with a first specific binding agent (in this case avidin labelled with a first fluorophore, for example, a first spectrally distinct QUANTUM DOT®, e.g., that emits at 585 mn) and a second specific binding agent (in this case an anti-DNP antibody, or antibody fragment, labelled with a second fluorophore (for example, a second spectrally distinct QUANTUM DOT®, e.g., that emits at 705 mn). Additional probes/binding agent pairs can be added to the multiplex detection scheme using other spectrally distinct fluorophores. Numerous variations of direct, and indirect (one step, two step or more) can be envisioned, all of which are suitable in the context of the disclosed probes and assays.

Probes typically comprise single-stranded nucleic acids of between 10 to 1000 nucleotides in length, for instance of between 10 and 800, more preferably of between 15 and 700, typically of between 20 and 500. Primers typically are shorter single-stranded nucleic acids, of between 10 to 25 nucleotides in length, designed to perfectly or almost perfectly match a nucleic acid of interest, to be amplified. The probes and primers are "specific" to the nucleic acids they hybridize to, i.e. they preferably hybridize under high stringency hybridization conditions (corresponding to the highest melting temperature Tm, e.g., 50% formamide, 5× or 6×SCC. SCC is a 0.15 M NaCl, 0.015 M Na-citrate).

The nucleic acid primers or probes used in the above amplification and detection method may be assembled as a kit. Such a kit includes consensus primers and molecular probes. A preferred kit also includes the components necessary to determine if amplification has occurred. The kit may also include, for example, PCR buffers and enzymes; positive control sequences, reaction control primers; and instructions for amplifying and detecting the specific sequences.

In some embodiments, the expression level of the lncRNA transcript is determined by DNA chip analysis. Such DNA chip or nucleic acid microarray consists of different nucleic acid probes that are chemically attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes comprise nucleic acids such as cDNAs or oligonucleotides that may be about 10 to about 60 base pairs. To determine the level, a sample from a test subject, optionally first subjected to a reverse transcription, is labelled and contacted with the microarray in hybridization conditions, leading to the formation of complexes between target nucleic acids that are complementary to probe sequences attached to the microarray surface. The labelled hybridized complexes are then detected and can be quantified or semi-quantified. Labelling may be achieved by various methods, e.g. by using radioactive or fluorescent labelling. Many variants of the microarray hybridization technology are available to the man skilled in the art (see e.g. the review by Hoheisel, Nature Reviews, Genetics, 2006, 7:200-210).

In some embodiments, the nCounter® Analysis system is used to detect intrinsic gene expression. The basis of the nCounter® Analysis system is the unique code assigned to each nucleic acid target to be assayed (International Patent Application Publication No. WO 08/124847, U.S. Pat. No. 8,415,102 and Geiss et al. Nature Biotechnology. 2008. 26(3): 317-325; the contents of which are each incorporated herein by reference in their entireties). The code is composed of an ordered series of colored fluorescent spots which create a unique barcode for each target to be assayed. A pair of probes is designed for each DNA or RNA target, a biotinylated capture probe and a reporter probe carrying the fluorescent barcode. This system is also referred to, herein, as the nanoreporter code system. Specific reporter and capture probes are synthesized for each target. The reporter probe can comprise at a least a first label attachment region to which are attached one or more label monomers that emit light constituting a first signal; at least a second label attachment region, which is non-overlapping with the first label attachment region, to which are attached one or more label monomers that emit light constituting a second signal; and a first target-specific sequence. Preferably, each sequence specific reporter probe comprises a target specific sequence capable of hybridizing to no more than one gene and optionally comprises at least three, or at least four label attachment regions, said attachment regions comprising one or more label monomers that emit light, constituting at least a third signal, or at least a fourth signal, respectively. The capture probe can comprise a second target-specific sequence; and a first affinity tag. In some embodiments, the capture probe can also comprise one or more label attachment regions. Preferably, the first target-specific sequence of the reporter probe and the second target-specific sequence of the capture probe hybridize to different regions of the same gene to be detected. Reporter and capture probes are all pooled into a single hybridization mixture, the "probe library". The relative abundance of each target is measured in a single multiplexed hybridization reaction. The method comprises contacting the tissue sample with a probe library, such that the presence of the target in the sample creates a probe pair-target complex. The complex is then purified. More specifically, the sample is combined with the probe library, and hybridization occurs in solution. After hybridization, the tripartite hybridized complexes (probe pairs and target) are purified in a two-step procedure using magnetic beads linked to oligonucleotides complementary to universal sequences present on the capture and reporter probes. This dual purification process allows the hybridization reaction to be driven to completion with a large excess of target-specific probes, as they are ultimately removed, and, thus, do not interfere with binding and imaging of the sample. All post hybridization steps are handled robotically on a custom liquid-handling robot (Prep Station, NanoString Technologies). Purified reactions are typically deposited by the Prep Station into individual flow cells of a sample cartridge, bound to a streptavidin-coated surface via the capture probe, electrophoresed to elongate the reporter probes, and immobilized. After processing, the sample cartridge is transferred to a fully automated imaging and data collection device (Digital Analyzer, NanoString Technologies). The level of a target is measured by imaging each sample and counting the number of times the code for that target is detected. For each sample, typically 600 fields-of-view (FOV) are imaged (1376×1024 pixels) representing approximately 10 mm2 of the binding surface. Typical imaging density is 100-1200 counted reporters per field of view depending on the degree of multiplexing, the amount of sample input, and overall target abundance. Data is output in simple spreadsheet format listing the number of counts per target, per sample. This system can be used along with nanoreporters. Additional disclosure regarding nanoreporters can be found in International Publication No. WO 07/076129 and WO07/076132, and US Patent Publication No. 2010/0015607 and 2010/0261026, the contents of which are incorporated herein in their entireties. Further, the term nucleic acid probes and nanoreporters can include the rationally designed (e.g. synthetic sequences) described in International Publication No. WO 2010/019826 and US Patent Publication No. 2010/0047924, incorporated herein by reference in its entirety.

In some embodiments, when multi-quantification is required, use of beads bearing binding partners of interest may be preferred. In some embodiments, the bead may be a cytometric bead for use in flow cytometry. Such beads may for example correspond to BD™ Cytometric Beads commercialized by BD Biosciences (San Jose, California). Typically cytometric beads may be suitable for preparing a multiplexed bead assay. A multiplexed bead assay, such as, for example, the BD™ Cytometric Bead Array, is a series of spectrally discrete beads that can be used to capture and quantify soluble antigens. Typically, beads are labelled with one or more spectrally distinct fluorescent dyes, and detection is carried out using a multiplicity of photodetectors, one for each distinct dye to be detected. A number of methods of making and using sets of distinguishable beads have been described in the literature. These include beads distinguishable by size, wherein each size bead is coated with a different target-specific antibody (see e.g. Fulwyler and McHugh, 1990, Methods in Cell Biology 33:613-629), beads with two or more fluorescent dyes at varying concentrations, wherein the beads are identified by the levels of fluorescence dyes (see e.g. European Patent No. 0 126,450), and beads distinguishably labelled with two different dyes, wherein the beads are identified by separately measuring the fluorescence intensity of each of the dyes (see e.g. U.S. Pat. Nos. 4,499,052 and 4,717,655). Both one-dimensional and two-dimensional arrays for the simultaneous analysis of multiple antigens by flow cytometry are available commercially. Examples of one-dimensional arrays of singly dyed beads distinguishable by the level of fluorescence intensity include the BD™ Cytometric Bead Array (CBA) (BD Biosciences, San Jose, Calif.) and Cyto-Plex™ Flow Cytometry microspheres (Duke Scientific, Palo Alto, Calif.). An example of a two-dimensional array of beads distinguishable by a combination of fluorescence intensity (five levels) and size (two sizes) is the QuantumPlex™ microspheres (Bangs Laboratories, Fisher, Ind.). An example of a two-dimensional array of doubly-dyed beads distinguishable by the levels of fluorescence of each of the two dyes is described in Fulton et al. (1997, Clinical Chemistry 43(9):1749-1756). The beads may be labelled with any fluorescent compound known in the art such as e.g. FITC (FL1), PE (FL2), fluorophores for use in the blue laser (e.g. PerCP, PE-Cy7, PE-Cy5, FL3 and APC or Cy5, FL4), fluorophores for use in the red, violet or UV laser (e.g. Pacific blue, pacific orange). In another particular embodiment, bead is a magnetic bead for use in magnetic separation. Magnetic beads are known to those of skill in the art. Typically, the magnetic bead is preferably made of a magnetic material selected from the group consisting of metals (e.g. ferrum, cobalt and nickel), an alloy thereof and an oxide thereof. In another particular embodiment, bead is bead that is dyed and magnetized.

In some embodiments, the expression level of the lncRNA transcript is determined by immunohistochemistry (IHC). Immunohistochemistry typically includes the following steps i) fixing said tissue sample with formalin, ii) embedding said tissue sample in paraffin, iii) cutting said tissue sample into sections for staining, iv) incubating said sections with the binding partner specific for the marker, v) rinsing said sections, vi) incubating said section with a biotinylated secondary antibody and vii) revealing the antigen-antibody complex with avidin-biotin-peroxidase complex. Accordingly, the tissue sample is firstly incubated the binding partners. After washing, the labeled antibodies that are bound to marker of interest are revealed by the appropriate technique, depending of the kind of label is borne by the labeled antibody, e.g. radioactive, fluorescent or enzyme label. Multiple labelling can be performed simultaneously. Alternatively, the method of the present invention may use a secondary antibody coupled to an amplification system (to intensify staining signal) and enzymatic molecules. Such coupled secondary antibodies are commercially available, e.g. from Dako, EnVision system. Counterstaining may be used, e.g. H&E, DAPI, Hoechst. Other staining methods may be accomplished using any suitable method or system as would be apparent to one of skill in the art, including automated, semi-automated or manual systems. For example, one or more labels can be attached to the antibody, thereby permitting detection of the target protein (i.e the marker). Exemplary labels include radioactive isotopes, fluorophores, ligands, chemiluminescent agents, enzymes, and combinations thereof. In some embodiments, the label is a quantum dot. Non-limiting examples of labels that can be conjugated to primary and/or secondary affinity ligands include fluorescent dyes or metals (e.g. fluorescein, rhodamine, phycoerythrin, fluorescamine), chromophoric dyes (e.g. rhodopsin), chemiluminescent compounds (e.g. luminal, imidazole) and bioluminescent proteins (e.g. luciferin, luciferase), haptens (e.g. biotin). A variety of other useful fluorescers and chromophores are described in Stryer L (1968) Science 162:526-533 and Brand L and Gohlke J R (1972) Annu. Rev. Biochem. 41:843-868. Affinity ligands can also be labeled with enzymes (e.g. horseradish peroxidase, alkaline phosphatase, beta-lactamase), radioisotopes (e.g. 3H, 14C, 32P, 35S or 125I) and particles (e.g. gold). The different types of labels can be conjugated to an affinity ligand using various chemistries, e.g. the amine reaction or the thiol reaction. However, other reactive groups than amines and thiols can be used, e.g. aldehydes, carboxylic acids and glutamine. Various enzymatic staining methods are known in the art for detecting a protein of interest. For example, enzymatic interactions can be visualized using different enzymes such as peroxidase, alkaline phosphatase, or different chromogens such as DAB, AEC or Fast Red. In other examples, the antibody can be conjugated to peptides or proteins that can be detected via a labeled binding partner or antibody. In an indirect IHC assay, a secondary antibody or second binding partner is necessary to detect the binding of the first binding partner, as it is not labeled. The resulting stained specimens are each imaged using a system for viewing the detectable signal and acquiring an image, such as a digital image of the staining. Methods for image acquisition are well known to one of skill in the art. For example, once the sample has been stained, any optical or non-optical imaging device can be used to detect the stain or biomarker label, such as, for example, upright or inverted optical microscopes, scanning confocal microscopes, cameras, scanning or tunneling electron microscopes, canning probe microscopes and imaging infrared detectors. In some examples, the image can be captured digitally. The obtained images can then be used for quantitatively or semi-quantitatively determining the amount of the marker in the sample. Various automated sample processing, scanning and analysis systems suitable for use with immunohistochemistry are available in the art. Such systems can include automated staining and microscopic scanning, computerized image analysis, serial section comparison (to control for variation in the orientation and size of a sample), digital report generation, and archiving and tracking of samples (such as slides on which tissue sections are placed). Cellular imaging systems are commercially available that combine conventional light microscopes with digital image processing systems to perform quantitative analysis on cells and tissues, including immunostained samples. See, e.g., the CAS-200 system (Becton, Dickinson & Co.). In particular, detection can be made manually or by image processing techniques involving computer processors and software. Using such software, for example, the images can be configured, calibrated, standardized and/or validated based on factors including, for example, stain quality or stain intensity, using procedures known to one of skill in the art (see e.g., published U.S. Patent Publication No. US20100136549). The image can be quantitatively or semi-quantitatively analyzed and scored based on staining intensity of the sample. Quantitative or semi-quantitative histochemistry refers to method of scanning and scoring samples that have undergone histochemistry, to identify and quantitate the presence of the specified biomarker (i.e. the marker). Quantitative or semi-quantitative methods can employ imaging software to detect staining densities or amount of staining or methods of detecting staining by the human eye, where a trained operator ranks results numerically. For example, images can be quantitatively analyzed using a pixel count algorithms (e.g., Aperio Spectrum Software, Automated QUantitatative Analysis platform (AQUA® platform), and other standard methods that measure or quantitate or semi-quantitate the degree of staining; see e.g., U.S. Pat. Nos. 8,023,714; 7,257,268; 7,219,016; 7,646,905; published U.S. Patent Publication No. US20100136549 and 20110111435; Camp et al. (2002) Nature Medicine, 8:1323-1327; Bacus et al. (1997) Analyt Quant Cytol Histol, 19:316-328). A ratio of strong positive stain (such as brown stain) to the sum of total stained area can be calculated and scored. The amount of the detected biomarker (i.e. the marker) is quantified and given as a percentage of positive pixels and/or a score. For example, the amount can be quantified as a percentage of positive pixels. In some examples, the amount is quantified as the percentage of area stained, e.g., the percentage of positive pixels. For example, a sample can have at least or about at least or about 0, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 40%, 45%, 50%, 55%, 60%, 65%, 70%, 75%, 80%, 85%, 90%, 95% or more positive pixels as compared to the total staining area. In some embodiments, a score is given to the sample that is a numerical representation of the intensity or amount of the histochemical staining of the sample, and represents the amount of target biomarker (e.g., the marker) present in the sample. Optical density or percentage area values can be given a scaled score, for example on an integer scale. Thus, in some embodiments, the method of the present invention comprises the steps consisting in i) providing one or more immunostained slices of tissue section obtained by an automated slide-staining system by using a binding partner capable of selectively interacting with the marker (e.g. an antibody as above descried), ii) proceeding to digitalisation of the slides of step a. by high resolution scan capture, iii) detecting the slice of tissue section on the digital picture iv) providing a size reference grid with uniformly distributed units having a same surface, said grid being adapted to the size of the tissue section to be analyzed, and v) detecting, quantifying and measuring intensity of stained cells in each unit whereby the number or the density of cells stained of each unit is assessed.

Multiplex tissue analysis techniques are particularly useful for quantifying several markers in the tissue sample. Such techniques should permit at least five, or at least ten or more biomarkers to be measured from a single tissue sample. Furthermore, it is advantageous for the technique to preserve the localization of the biomarker and be capable of distinguishing the presence of biomarkers in cancerous and non-cancerous cells. Such methods include layered immunohistochemistry (L-IHC), layered expression scanning (LES) or multiplex tissue immunoblotting (MTI) taught, for example, in U.S. Pat. Nos. 6,602,661, 6,969,615, 7,214,477 and 7,838,222; U.S. Publ. No. 2011/0306514 (incorporated herein by reference); and in Chung & Hewitt, Meth Mol Biol, Prot Blotting Detect, Kurlen & Scofield, eds. 536: 139-148, 2009, each reference teaches making up to 8, up to 9, up to 10, up to 11 or more images of a tissue section on layered and blotted membranes, papers, filters and the like, can be used. Coated membranes useful for conducting the L-IHC/MTI process are available from 20/20 GeneSystems, Inc. (Rockville, MD).

In some embodiments, the L-IHC method can be performed on any of a variety of tissue samples, whether fresh or preserved. The samples included core needle biopsies that were routinely fixed in 10% normal buffered formalin and processed in the pathology department. Standard five μιη thick tissue sections were cut from the tissue blocks onto charged slides that were used for L-IHC. Thus, L-IHC enables testing of multiple markers in a tissue section by obtaining copies of molecules transferred from the tissue section to plural bioaffinity-coated membranes to essentially produce copies of tissue "images." In the case of a paraffin section, the tissue section is deparaffinized as known in the art, for example, exposing the section to xylene or a xylene substitute such as NEO-CLEAR®, and graded ethanol solutions. The section can be treated with a proteinase, such as, papain, trypsin, proteinase K and the like. Then, a stack of a membrane substrate comprising, for example, plural sheets of a 10μιη thick coated polymer backbone with 0.4μιη diameter pores to channel tissue molecules, such as, proteins, through the stack, then is placed on the tissue section. The movement of fluid and tissue molecules is configured to be essentially perpendicular to the membrane surface. The sandwich of the section, membranes, spacer papers, absorbent papers, weight and so on can be exposed to heat to facilitate movement of molecules from the tissue into the membrane stack. A portion of the proteins of the tissue are captured on each of the bioaffinity-coated membranes of the stack (available from 20/20 GeneSystems, Inc., Rockville, MD). Thus, each membrane comprises a copy of the tissue and can be probed for a different biomarker using standard immunoblotting techniques, which enables open-ended expansion of a marker profile as performed on a single tissue section. As the amount of protein can be lower on membranes more distal in the stack from the tissue, which can arise, for example, on different amounts of molecules in the tissue sample, different mobility of molecules released from the tissue sample, different binding affinity of the molecules to the membranes, length of transfer and so on, normalization of values, running controls, assessing transferred levels of tissue molecules and the like can be included in the procedure to correct for changes that occur within, between and among membranes and to enable a direct comparison of information within, between and among membranes. Hence, total protein can be determined per membrane using, for example, any means for quantifying protein, such as, biotinylating available molecules, such as, proteins, using a standard reagent and method, and then revealing the bound biotin by exposing the membrane to a labeled avidin or streptavidin; a protein stain, such as, Blot fastStain, Ponceau Red, brilliant blue stains and so on, as known in the art.

In some embodiments, the present methods utilize Multiplex Tissue Imprinting (MTI) technology for measuring biomarkers, wherein the method conserves precious biopsy tissue by allowing multiple biomarkers, in some cases at least six biomarkers.

In some embodiments, alternative multiplex tissue analysis systems exist that may also be employed as part of the present invention. One such technique is the mass spectrometry-based Selected Reaction Monitoring (SRM) assay system ("Liquid Tissue" available from OncoPlexDx (Rockville, MD). That technique is described in U.S. Pat. No. 7,473,532.

In some embodiments, the method of the present invention utilized the multiplex IHC technique developed by GE Global Research (Niskayuna, NY). That technique is described in U.S. Pub. Nos. 2008/0118916 and 2008/0118934. There, sequential analysis is performed on biological samples containing multiple targets including the steps of binding a fluorescent probe to the sample followed by signal detection, then inactivation of the probe followed by binding probe to another target, detection and inactivation, and continuing this process until all targets have been detected.

In some embodiments, multiplex tissue imaging can be performed when using fluorescence (e.g. fluorophore or Quantum dots) where the signal can be measured with a multispectral imagine system. Multispectral imaging is a technique in which spectroscopic information at each pixel of an image is gathered and the resulting data analyzed with spectral image-processing software. For example, the system can take a series of images at different wavelengths that are electronically and continuously selectable and then utilized with an analysis program designed for handling such data. The system can thus be able to obtain quantitative information from multiple dyes simultaneously, even when the spectra of the dyes are highly overlapping or when they are co-localized, or occurring at the same point in the sample, provided that the spectral curves are different. Many biological materials auto fluoresce, or emit lower-energy light when excited by higher-energy light. This signal can result in lower contrast images and data. High-sensitivity cameras without multispectral imaging capability only increase the autofluorescence signal along with the fluorescence signal. Multispectral imaging can unmix, or separate out, autofluorescence from tissue and, thereby, increase the achievable signal-to-noise ratio. Briefly the quantification can be performed by following steps: i) providing a tumor tissue microarray (TMA) obtained from the subject, ii) TMA samples are then stained with anti-antibodies having specificity of the protein(s) of interest, iii) the TMA slide is further stained with an epithelial cell marker to assist in automated segmentation of tumour and stroma, iv) the TMA slide is then scanned using a multispectral imaging system, v) the scanned images are processed using an automated image analysis software (e.g. Perkin Elmer Technology) which allows the detection, quantification and segmentation of specific tissues through powerful pattern recognition algorithms. The machine-learning algorithm was typically previously trained to segment tumor from stroma and identify cells labelled.

In some embodiments, the method of the present invention further comprises comparing the expression level of the LINC01087 of the invention with a predetermined reference value wherein detecting a difference between the expression level of the genes of the invention and the predetermined reference value indicates whether the subject is or is not at risk of having a breast cancer.

In some embodiments, the predetermined reference value is a relative to a number or value derived from population studies, including without limitation, subjects of the same or similar age range, subjects in the same or similar ethnic group, and subjects having the same severity of lesion. Such predetermined reference values can be derived from statistical analyses and/or risk prediction data of populations obtained from mathematical algorithms and computed indices. In some embodiments, retrospective measurement of the level of the marker in properly banked historical subject samples may be used in establishing these predetermined reference values. Accordingly, in some embodiments, the predetermined reference value is a threshold value or a cut-off value. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. For example, after determining the level of the marker in a group of reference (e.g. healthy breast tissue), one can use algorithmic analysis for the statistic treatment of the measured levels of the marker in samples to be tested, and thus obtain a classification standard having significance for sample classification. The full name of ROC curve is receiver operator characteristic curve, which is also known as receiver operation characteristic curve. It is mainly used for clinical biochemical diagnostic tests. ROC curve is a comprehensive indicator that reflects the continuous variables of true positive rate (sensitivity) and false positive rate (1-specificity). It reveals the relationship between sensitivity and specificity with the image composition method. A series of different cut-off values (thresholds or critical values, boundary values between normal and abnormal results of diagnostic test) are set as continuous variables to calculate a series of sensitivity and specificity values. Then sensitivity is used as the vertical coordinate and specificity is used as the horizontal coordinate to draw a curve. The higher the area under the curve (AUC), the higher the accuracy of diagnosis. On the ROC curve, the point closest to the far upper left of the coordinate diagram is a critical point having both high sensitivity and high specificity values. The AUC value of the ROC curve is between 1.0 and 0.5. When AUC>0.5, the diagnostic result gets better and better as AUC approaches 1. When AUC is between 0.5 and 0.7, the accuracy is low. When AUC is between 0.7 and 0.9, the accuracy is moderate. When AUC is higher than 0.9, the accuracy is quite high. This algorithmic method is preferably done with a computer. Existing software or systems in the art may be used for the drawing of the ROC curve, such as: MedCalc 9.2.0.1 medical statistical software, SPSS 9.0, ROCPOWER.SAS, DESIGNROC.FOR, MULTIREADER POWER.SAS, CREATE-ROC.SAS, GB STAT VI0.0 (Dynamic Microsystems, Inc. Silver Spring, Md., USA), etc.

In some embodiments, a score which is a composite of several different genes is determined and compared to the predetermined reference value wherein a difference between said score and said predetermined reference value is indicative whether the subject has or is at risk of having a breast cancer (e.g. TNBC or luminal BC subtypes).

In some embodiments, the method of the invention comprises the use of a classification algorithm typically selected from Linear Discriminant Analysis (LDA), Topological Data Analysis (TDA), Neural Networks, Support Vector Machine (SVM) algorithm and Random Forests algorithm (RF). In some embodiments, the method of the invention comprises the step of determining the subject response using a classification algorithm. As used herein, the term "classification algorithm" has its general meaning in the art and refers to classification and regression tree methods and multivariate classification well known in the art such as described in U.S. Pat. No. 8,126,690; WO2008/156617. As used herein, the term "support vector machine (SVM)" is a universal learning machine useful for pattern recognition, whose decision surface is parameterized by a set of support vectors and a set of corresponding weights, refers to a method of not separately processing, but simultaneously processing a plurality of variables. Thus, the support vector machine is useful as a statistical tool for classification. The support vector machine non-linearly maps its n-dimensional input space into a high dimensional feature space, and presents an optimal interface (optimal parting plane) between features. The support vector machine comprises two phases: a training phase and a testing phase. In the training phase, support vectors are produced, while estimation is performed according to a specific rule in the testing phase. In general, SVMs provide a model for use in classifying each of n subjects to two or more disease categories based on one k-dimensional vector (called a k-tuple) of biomarker measurements per subject. A SVM first transforms the k-tuples using a kernel function into a space of equal or higher dimension. The kernel function projects the data into a space where the categories can be better separated using hyperplanes than would be possible in the original data space. To determine the hyperplanes with which to discriminate between categories, a set of support vectors, which lie closest to the boundary between the disease categories, may be chosen. A hyperplane is then selected by known SVM techniques such that the distance between the support vectors and the hyperplane is maximal within the bounds of a cost function that penalizes incorrect predictions. This hyperplane is the one which optimally separates the data in terms of prediction (Vapnik, 1998 Statistical Learning Theory. New York: Wiley). Any new observation is then classified as belonging to any one of the categories of interest, based where the observation lies in relation to the hyperplane. When more than two categories are considered, the process is carried out pairwise for all of the categories and those results combined to create a rule to discriminate between all the categories. As used herein, the term "Random Forests algorithm" or "RF" has its general meaning in the art and refers to classification algorithm such as described in U.S. Pat. No. 8,126,690; WO2008/156617. Random Forest is a decision-tree-based classifier that is constructed using an algorithm originally developed by Leo Breiman (Breiman L, "Random forests," Machine Learning 2001, 45:5-32). The classifier uses a large number of individual decision trees and decides the class by choosing the mode of the classes as determined by the individual trees. The individual trees are constructed using the following algorithm: (1) Assume that the number of cases in the training set is N, and that the number of variables in the classifier is M; (2) Select the number of input variables that will be used to determine the decision at a node of the tree; this number, m should be much less than M; (3) Choose a training set by choosing N samples from the training set with replacement; (4) For each node of the tree randomly select m of the M variables on which to base the decision at that node; (5) Calculate the best split based on these m variables in the training set. In some embodiments, the score is generated by a computer program.

In some embodiments, the method of the present invention comprises a) quantifying the level of a plurality of markers in the sample; b) implementing a classification algorithm on data comprising the quantified plurality of markers so as to obtain an algorithm output; c) determining the probability that the subject will develop a cancer from the algorithm output of step b).

The algorithm of the present invention can be performed by one or more programmable processors executing one or more computer programs to perform functions by operating on input data and generating output. The algorithm can also be performed by, and apparatus can also be implemented as, special purpose logic circuitry, e.g., an FPGA (field programmable gate array) or an ASIC (application-specific integrated circuit). Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device. Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry. To provide for interaction with a user, embodiments of the invention can be implemented on a computer having a display device, e.g., in non-limiting examples, a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. Accordingly, in some embodiments, the algorithm can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the invention, or any combination of one or more such back-end, middleware, or front-end components. The components of the system can be interconnected by any form or medium of digital data communication, e.g., a communication network. Examples of communication networks include a local area network ("LAN") and a wide area network ("WAN"), e.g., the Internet. The computing system can include clients and servers. A client and server are generally remote from each other and typically interact through a communication network. The relationship of client and server arises by virtue of computer programs running on the respective computers and having a client-server relationship to each other.

The inventors also show that BC patients harbouring alterations in TP53 gene present LINC01087 strongly downregulated comparing to TP53 wild-type patients. However, they further demonstrate that this correlation between TP53 mutation and LINC01087 expression actually resulted from a dominance of TNBC subtypes in the mutated cohort. In this line, TP53 mutated BCs harbouring high levels of LINC01087 belonged to the luminal subtypes.

As used herein, the term "TP53 gene" or "tumor protein p53" has its general meaning in the art and refers to a tumor suppressor gene involved in the development of many human cancers and plays a major role in the stress response. TP53 gene is a transcription factor that controls the expression of many genes involved in apoptosis and cell cycle regulation. The TP53 gene has a nucleotide sequence having the following number: Gene ID: 7157.

The inventors also show that BC patients harbouring alterations in BRCA1 gene present LINC01087 strongly downregulated comparing to BRCA1 wild-type patients. However, they further demonstrate that this correlation between BRCA1 mutation and LINC01087 expression actually resulted from a dominance of TNBC subtypes in the mutated cohort.

As used herein, the term "BRCA1" has is general meaning in the art and is normally expressed in the cells of breast and other tissue, where it help to repair damaged DNA, or destroy cells if DNA cannot be repaired. BRCA1 is involved in the repair of chromosomal damage with an important role in the error-free repair of DNA double-strand breaks. If BRCA1 is damaged by a BRCA mutation, damaged DNA is not repaired properly, and this increases the risk for breast cancer. BRCA1 is also known as "breast cancer susceptibility gene" and "breast cancer susceptibility protein". The BRCA1 gene has a nucleotide sequence having the following number: Gene ID: 672.

Method for Managing Breast Cancer Treatment

Accordingly, the method of the present invention is also suitable for determining whether a subject suffering from breast cancer is eligible for a treatment or even for surgery.

As used herein the term “surgery” has is general meaning in the art and refers to the removal of the tumor and some surrounding healthy tissue during an operation. Surgery is also used to examine the nearby axillary lymph nodes, which are under the arm.

The types of surgery include the following:

- Lumpectomy which is the removal of the tumor and a small, cancer-free margin of healthy tissue around the tumor. Most of the breast remains. For invasive cancer, radiation therapy to the remaining breast tissue is generally recommended after surgery. For DCIS, radiation therapy after surgery may be an option depending on the patient and the tumor. A lumpectomy may also be called breast-conserving surgery, a partial mastectomy, quadrantectomy, or a segmental mastectomy.
- Mastectomy which is the surgical removal of the entire breast.

The invention relates to a method for treating a subject suffering from breast cancer, wherein said method comprises the step of determining in a sample obtained from said subject the expression level of LINC01087.

The invention relates to a method for treating a subject suffering from TNBC, wherein said method comprises the step of:

(i) Determining in a sample obtained from said subject the expression level of LINC01087
(ii) Comparing the expression levels determined at step i) with a predetermined reference value and
(iii) Administering to said subject a therapeutically effective amount of a radiotherapeutic agent and/or an immunotherapeutic agent and/or a chemotherapeutic agent and/or hormonotherapy if the expression level of LINC01087 is lower than the predetermined reference value.

The invention relates to a method for treating a subject suffering from luminal BC subtypes, wherein said method comprises the step of:

(i) Determining in a sample obtained from said subject the expression level of LINC01087
(ii) Comparing the expression levels determined at step i) with a predetermined reference value and
(iii) Administering to said subject a therapeutically effective amount of a radiotherapeutic agent and/or an immunotherapeutic agent and/or a chemotherapeutic agent and/or hormonotherapy if the expression level of LINC01087 is higher than the predetermined reference value.

As used herein, the terms “treating” or “treatment” refer to both prophylactic or preventive treatment as well as curative or disease modifying treatment, including treatment of subject at risk of contracting the disease or suspected to have contracted the disease as well as subject who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By “therapeutic regimen” is meant the pattern of treatment of an illness, e.g., the pattern of dosing used during therapy. A therapeutic regimen may include an induction regimen and a maintenance regimen. The phrase “induction regimen” or “induction period” refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a “loading regimen”, which may include administering a greater dose of the drug than a physician would employ during a maintenance regimen, administering a drug more frequently than a physician would administer the drug during a maintenance regimen, or both. The phrase “maintenance regimen” or “maintenance period” refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., pain, disease manifestation, etc.]).

In some embodiments, the treatment consists of administering to the subject a targeted cancer therapy. Targeted cancer therapies are drugs or other substances that block the growth and spread of cancer by interfering with specific molecules (“molecular targets”) that are involved in the growth, progression, and spread of cancer. Targeted cancer therapies are sometimes called “molecularly targeted drugs,” “molecularly targeted therapies,” “precision medicines,” or similar names.

In some embodiments, the treatment consists of administering to the subject a radiotherapeutic agent. The term “radiotherapeutic agent” as used herein, is intended to refer to any radiotherapeutic agent known to one of skill in the art to be effective to treat or ameliorate cancer, without limitation. For instance, the radiotherapeutic agent can be an agent such as those administered in brachytherapy or radionuclide therapy. Such methods can optionally further comprise the administration of one or more additional cancer therapies, such as, but not limited to, chemotherapies, and/or another radiotherapy.

In some embodiment, the radiotherapy consists of proton therapy or proton radiotherapy. The term “proton therapy” or “proton radiotherapy” refers to a type of particle therapy that uses a beam of protons to irradiate diseased tissue, most often in the treatment of cancer. The chief advantage of proton therapy over other types of external beam radiotherapy is that as a charged particle the dose is deposited over a narrow range of depth, and there is minimal entry, exit, or scattered radiation dose.

In some embodiments, the treatment consists of administering to the subject a chemotherapeutic agent. The term “chemotherapeutic agent” refers to chemical compounds that are effective in inhibiting tumor growth. Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaorarnide and trimethylolomelamine; acetogenins (especially bullatacin and bullatacinone); a carnptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estrarnustine, ifosfamide, mechlorethamine, mechlorethamine oxide hydrochloride, melphalan, novembichin, phenesterine, prednimus tine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin (11 and calicheamicin 211, see, e.g., Agnew Chem Intl. Ed. Engl. 33: 183-186 (1994); dynemicin, including dynemicin A; an esperamicin; as well as neocarzinostatin chromophore and related chromoprotein enediyne antiobiotic chromomophores), aclacinomysins, actinomycin, authramycin, azaserine, bleomycins, cactinomycin, carabicin, canninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idanrbicin, marcellomycin, mitomycins, mycophenolic acid, nogalarnycin, olivomycins, peplomycin, potfiromycin, puromycin, quelamycin, rodorubicin, streptomgrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophospharnide glycoside; aminolevulinic acid; amsacrine; bestrabucil; bisantrene; edatraxate; defo famine; demecolcine; diaziquone; elfornithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pento statin; phenamet; pirarubicin; podophyllinic acid; 2-ethylhydrazide; procarbazine; PSK®; razoxane; rhizoxin; sizofiran; spirogennanium; tenuazonic acid; triaziquone; 2,2',2"-trichlorotriethylarnine; trichothecenes (especially T-2 toxin, verracurin A, roridinA and anguidine); urethan; vindesine; dacarbazine; mannomustine; mitobromtol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.].) and doxetaxel (TAXOTERE®, Rhone-Poulenc Rorer, Antony, France); chlorambucil; gemcitabine; 6-thioguanine; mercaptopurine; methotrexate; platinum analogs such as cisp latin and carbop latin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-1 1; topoisomerase inhibitor RFS 2000; difluoromethylornithine (DMFO); retinoic acid; capecitabine; and pharmaceutically acceptable salts, acids or derivatives of any of the above. Also included in this definition are antihormonal agents that act to regulate or inhibit honnone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

In some embodiments, the treatment consists of administering to the subject an immunotherapeutic agent. The term "immunotherapeutic agent," as used herein, refers to a compound, composition or treatment that indirectly or directly enhances, stimulates or increases the body's immune response against cancer cells and/or that decreases the side effects of other anticancer therapies. Immunotherapy is thus a therapy that directly or indirectly stimulates or enhances the immune system's responses to cancer cells and/or lessens the side effects that may have been caused by other anti-cancer agents. Immunotherapy is also referred to in the art as immunologic therapy, biological therapy biological response modifier therapy and biotherapy. Examples of common immunotherapeutic agents known in the art include, but are not limited to, cytokines, cancer vaccines, monoclonal antibodies and non-cytokine adjuvants. Alternatively the immunotherapeutic treatment may consist of administering the subject with an amount of immune cells (T cells, NK, cells, dendritic cells, B cells . . . ).

Immunotherapeutic agents can be non-specific, i.e. boost the immune system generally so that the human body becomes more effective in fighting the growth and/or spread of cancer cells, or they can be specific, i.e. targeted to the cancer cells themselves immunotherapy regimens may combine the use of non-specific and specific immunotherapeutic agents.

Non-specific immunotherapeutic agents are substances that stimulate or indirectly improve the immune system. Non-specific immunotherapeutic agents have been used alone as a main therapy for the treatment of cancer, as well as in addition to a main therapy, in which case the non-specific immunotherapeutic agent functions as an adjuvant to enhance the effectiveness of other therapies (e.g. cancer vaccines). Non-specific immunotherapeutic agents can also function in this latter context to reduce the side effects of other therapies, for example, bone marrow suppression induced by certain chemotherapeutic agents. Non-specific immunotherapeutic agents can act on key immune system cells and cause secondary responses, such as increased production of cytokines and immunoglobulins. Alternatively, the agents can themselves comprise cytokines. Non-specific immunotherapeutic agents are generally classified as cytokines or non-cytokine adjuvants.

A number of cytokines have found application in the treatment of cancer either as general non-specific immunotherapies designed to boost the immune system, or as adjuvants provided with other therapies. Suitable cytokines include, but are not limited to, interferons, interleukins and colony-stimulating factors.

Interferons (IFNs) contemplated by the present invention include the common types of IFNs, IFN-alpha (IFN-$\alpha$), IFN-beta (IFN-$\beta$) and IFN-gamma (IFN-$\gamma$). IFNs can act directly on cancer cells, for example, by slowing their growth, promoting their development into cells with more normal behaviour and/or increasing their production of antigens thus making the cancer cells easier for the immune system to recognise and destroy. IFNs can also act indirectly on cancer cells, for example, by slowing down angiogenesis, boosting the immune system and/or stimulating natural killer (NK) cells, T cells and macrophages. Recombinant IFN-alpha is available commercially as Roferon (Roche Pharmaceuticals) and Intron A (Schering Corporation).

Interleukins contemplated by the present invention include IL-2, IL-4, IL-11 and IL-12. Examples of commercially available recombinant interleukins include Proleukin® (IL-2; Chiron Corporation) and Neumega® (IL-12; Wyeth Pharmaceuticals). Zymogenetics, Inc. (Seattle, Wash.) is currently testing a recombinant form of IL-21, which is also contemplated for use in the combinations of the present invention.

Colony-stimulating factors (CSFs) contemplated by the present invention include granulocyte colony stimulating factor (G-CSF or filgrastim), granulocyte-macrophage colony stimulating factor (GM-CSF or sargramostim) and erythropoietin (epoetin alfa, darbepoietin). Treatment with one or more growth factors can help to stimulate the generation of new blood cells in subjects undergoing traditional chemotherapy. Accordingly, treatment with CSFs can be helpful in decreasing the side effects associated with chemotherapy and can allow for higher doses of chemotherapeutic agents to be used. Various-recombinant colony stimulating factors are available commercially, for example, Neupogen® (G-CSF; Amgen), Neulasta (pelfilgrastim; Amgen), Leukine (GM-CSF; Berlex), Procrit (erythropoietin; Ortho Biotech), Epogen (erythropoietin; Amgen), Arnesp (erytropoietin).

In addition to having specific or non-specific targets, immunotherapeutic agents can be active, i.e. stimulate the body's own immune response, or they can be passive, i.e. comprise immune system components that were generated external to the body.

Passive specific immunotherapy typically involves the use of one or more monoclonal antibodies that are specific for a particular antigen found on the surface of a cancer cell or that are specific for a particular cell growth factor. Monoclonal antibodies may be used in the treatment of cancer in a number of ways, for example, to enhance a subject's immune response to a specific type of cancer, to interfere with the growth of cancer cells by targeting specific cell growth factors, such as those involved in angiogenesis, or by enhancing the delivery of other anticancer agents to cancer cells when linked or conjugated to agents such as chemotherapeutic agents, radioactive particles or toxins.

In some embodiments, the immunotherapeutic agent is an immune checkpoint inhibitor.

In some embodiments, the targeted therapy consists of administering the subject with an immune checkpoint inhibitor.

As used herein, the term "immune checkpoint inhibitor" refers to molecules that totally or partially reduce, inhibit, interfere with or modulate one or more immune checkpoint proteins. As used herein, the term "immune checkpoint protein" has its general meaning in the art and refers to a molecule that is expressed by T cells in that either turn up a signal (stimulatory checkpoint molecules) or turn down a signal (inhibitory checkpoint molecules). Immune checkpoint molecules are recognized in the art to constitute immune checkpoint pathways similar to the CTLA-4 and PD-1 dependent pathways (see e.g. Pardoll, 2012. Nature Rev Cancer 12:252-264; Mellman et al. 2011. Nature 480: 480-489). Examples of stimulatory checkpoint include CD27 CD28 CD40, CD122, CD137, OX40, GITR, and ICOS. Examples of inhibitory checkpoint molecules include A2AR, B7-H3, B7-H4, BTLA, CTLA-4, CD277, IDO, KIR, PD-1, LAG-3, TIM-3 and VISTA. The Adenosine A2A receptor (A2AR) is regarded as an important checkpoint in cancer therapy because adenosine in the immune microenvironment, leading to the activation of the A2a receptor, is negative immune feedback loop and the tumor microenvironment has relatively high concentrations of adenosine. B7-H3, also called CD276, was originally understood to be a co-stimulatory molecule but is now regarded as co-inhibitory. B7-H4, also called VTCN1, is expressed by tumor cells and tumor-associated macrophages and plays a role in tumour escape. B and T Lymphocyte Attenuator (BTLA) and also called CD272, has HVEM (Herpesvirus Entry Mediator) as its ligand. Surface expression of BTLA is gradually downregulated during differentiation of human CD8+ T cells from the naive to effector cell phenotype, however tumor-specific human CD8+ T cells express high levels of BTLA. CTLA-4, Cytotoxic T-Lymphocyte-Associated protein 4 and also called CD152. Expression of CTLA-4 on Treg cells serves to control T cell proliferation. IDO, Indoleamine 2,3-dioxygenase, is a tryptophan catabolic enzyme. A related immune-inhibitory enzymes. Another important molecule is TDO, tryptophan 2,3-dioxygenase. IDO is known to suppress T and NK cells, generate and activate Tregs and myeloid-derived suppressor cells, and promote tumour angiogenesis. KIR, Killer-cell Immunoglobulin-like Receptor, is a receptor for MHC Class I molecules on Natural Killer cells. LAG3, Lymphocyte Activation Gene-3, works to suppress an immune response by action to Tregs as well as direct effects on CD8+ T cells. PD-1, Programmed Death 1 (PD-1) receptor, has two ligands, PD-L1 and PD-L2. This checkpoint is the target of Merck & Co.'s melanoma drug Keytruda, which gained FDA approval in September 2014. An advantage of targeting PD-1 is that it can restore immune function in the tumor microenvironment. TIM-3, short for T-cell Immunoglobulin domain and Mucin domain 3, expresses on activated human CD4+ T cells and regulates Th1 and Th17 cytokines. TIM-3 acts as a negative regulator of Th1/Tc1 function by triggering cell death upon interaction with its ligand, galectin-9. VISTA, Short for V-domain Ig suppressor of T cell activation, VISTA is primarily expressed on hematopoietic cells so that consistent expression of VISTA on leukocytes within tumors may allow VISTA blockade to be effective across a broad range of solid tumors. Tumor cells often take advantage of these checkpoints to escape detection by the immune system. Thus, inhibiting a checkpoint protein on the immune system may enhance the anti-tumor T-cell response.

In some embodiments, an immune checkpoint inhibitor refers to any compound inhibiting the function of an immune checkpoint protein. Inhibition includes reduction of function and full blockade. In some embodiments, the immune checkpoint inhibitor could be an antibody, synthetic or native sequence peptides, small molecules or aptamers which bind to the immune checkpoint proteins and their ligands.

In a particular embodiment, the immune checkpoint inhibitor is an antibody.

Typically, antibodies are directed against A2AR, B7-H3, B7-H4, BTLA, CTLA-4, CD277, IDO, KIR, PD-1, LAG-3, TIM-3 or VISTA.

In a particular embodiment, the immune checkpoint inhibitor is an anti-PD-1 antibody such as described in WO2011082400, WO2006121168, WO2015035606, WO2004056875, WO2010036959, WO2009114335, WO2010089411, WO2008156712, WO2011110621, WO2014055648 and WO2014194302. Examples of anti-PD-1 antibodies which are commercialized: Nivolumab (Opdivo®, BMS), Pembrolizumab (also called Lambrolizumab, KEYTRUDA® or MK-3475, MERCK).

In some embodiments, the immune checkpoint inhibitor is an anti-PD-L1 antibody such as described in WO2013079174, WO2010077634, WO2004004771, WO2014195852, WO2010036959, WO2011066389, WO2007005874, WO2015048520, U.S. Pat. No. 8,617,546 and WO2014055897. Examples of anti-PD-L1 antibodies which are on clinical trial: Atezolizumab (MPDL3280A, Genentech/Roche), Durvalumab (AZD9291, AstraZeneca), Avelumab (also known as MSB0010718C, Merck) and BMS-936559 (BMS).

In some embodiments, the immune checkpoint inhibitor is an anti-PD-L2 antibody such as described in U.S. Pat. Nos. 7,709,214, 7,432,059 and 8,552,154.

In the context of the invention, the immune checkpoint inhibitor inhibits Tim-3 or its ligand.

In a particular embodiment, the immune checkpoint inhibitor is an anti-Tim-3 antibody such as described in WO03063792, WO2011155607, WO2015117002, WO2010117057 and WO2013006490.

In some embodiments, the immune checkpoint inhibitor is a small organic molecule.

The term "small organic molecule" as used herein, refers to a molecule of a size comparable to those organic molecules generally used in pharmaceuticals. The term excludes biological macro molecules (e. g. proteins, nucleic acids, etc.). Typically, small organic molecules range in size up to about 5000 Da, more preferably up to 2000 Da, and most preferably up to about 1000 Da.

Typically, the small organic molecules interfere with transduction pathway of A2AR, B7-H3, B7-H4, BTLA, CTLA-4, CD277, IDO, KIR, PD-1, LAG-3, TIM-3 or VISTA.

In a particular embodiment, small organic molecules interfere with transduction pathway of PD-1 and Tim-3. For example, they can interfere with molecules, receptors or enzymes involved in PD-1 and Tim-3 pathway.

In a particular embodiment, the small organic molecules interfere with Indoleamine-pyrrole 2,3-dioxygenase (IDO) inhibitor. IDO is involved in the tryptophan catabolism (Liu et al 2010, Vacchelli et al 2014, Zhai et al 2015). Examples of IDO inhibitors are described in WO 2014150677. Examples of IDO inhibitors include without limitation 1-methyl-tryptophan (IMT), β-(3-benzofuranyl)-alanine, β-(3-benzo(b)thienyl)-alanine), 6-nitro-tryptophan, 6-fluoro-tryptophan, 4-methyl-tryptophan, 5-methyl tryptophan, 6-methyl-tryptophan, 5-methoxy-tryptophan, 5-hydroxy-tryptophan, indole 3-carbinol, 3,3'-diindolylmethane, epigallocatechin gallate, 5-Br-4-Cl-indoxyl 1,3-diacetate, 9-vinylcarbazole, acemetacin, 5-bromo-tryptophan, 5-bromoindoxyl diacetate, 3-Amino-naphtoic acid, pyrrolidine dithiocarbamate, 4-phenylimidazole a brassinin derivative, a thiohydantoin derivative, a β-carboline derivative or a brassilexin derivative. In a particular embodiment, the IDO inhibitor is selected from 1-methyl-tryptophan, β-(3-benzofuranyl)-alanine, 6-nitro-L-tryptophan, 3-Amino-naphtoic acid and β-[3-benzo(b)thienyl]-alanine or a derivative or prodrug thereof.

In a particular embodiment, the inhibitor of IDO is Epacadostat, (INCB24360, INCB024360) has the following chemical formula in the art and refers to —N-(3-bromo-4-fluorophényl)-N'-hydroxy-4-{[2-(sulfamoylamino)-éthyl] amino}-1,2,5-oxadiazole-3 carboximidamide:

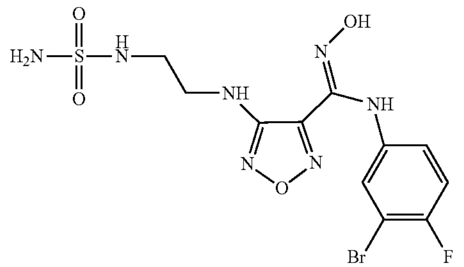 [SMILES: NS(=O)(=O)NCCNc1nonc1/C(=N/O)Nc1ccc(F)c(Br)c1]

In a particular embodiment, the inhibitor is BGB324, also called R428, such as described in WO2009054864, refers to 1H-1,2,4-Triazole-3,5-diamine, 1-(6,7-dihydro-5H-benzo[6,7]cyclohepta[1,2-c]pyridazin-3-yl)-N3-[(7S)-6,7,8,9-tetrahydro-7-(1-pyrrolidinyl)-5H-benzocyclohepten-2-yl]- and has the following formula in the art:

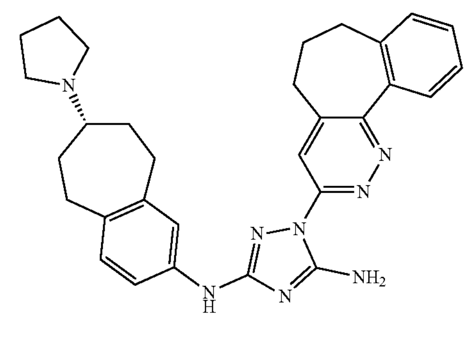 [SMILES: Nc1nc(Nc2ccc3c(c2)CC[C@@H](N2CCCC2)CC3)nn1-c1cc2c(nn1)-c1ccccc1CCC2]

In a particular embodiment, the inhibitor is CA-170 (or AUPM-170): an oral, small molecule immune checkpoint antagonist targeting programmed death ligand-1 (PD-L1) and V-domain Ig suppressor of T cell activation (VISTA) (Liu et al 2015). Preclinical data of CA-170 are presented by Curis Collaborator and Aurigene on November at ACR-NCI-EORTC International Conference on Molecular Targets and Cancer Therapeutics.

In some embodiments, the immune checkpoint inhibitor is an aptamer.

Typically, the aptamers are directed against A2AR, B7-H3, B7-H4, BTLA, CTLA-4, CD277, IDO, KIR, PD-1, LAG-3, TIM-3 or VISTA.

In a particular embodiment, aptamers are DNA aptamers such as described in Prodeus et al 2015. A major disadvantage of aptamers as therapeutic entities is their poor pharmacokinetic profiles, as these short DNA strands are rapidly removed from circulation due to renal filtration. Thus, aptamers according to the invention are conjugated to with high molecular weight polymers such as polyethylene glycol (PEG). In a particular embodiment, the aptamer is an anti-PD-1 aptamer. Particularly, the anti-PD-1 aptamer is MP7 pegylated as described in Prodeus et al 2015.

In some embodiment, the surgery is combined with a therapeutic treatment.

In some embodiment, the surgery is combined with a radiotherapeutic agent and/or an immunotherapeutic agent and/or a chemotherapeutic agent.

As used herein, the term "combination" is intended to refer to all forms of administration that provide a first drug together with a further (second, third . . . ) drug. The drugs may be administered simultaneous, separate or sequential and in any order. According to the invention, the drug is administered to the subject using any suitable method that enables the drug to reach the lungs. In some embodiments, the drug administered to the subject systemically (i.e. via systemic administration). Thus, in some embodiments, the drug is administered to the subject such that it enters the circulatory system and is distributed throughout the body. In some embodiments, the drug is administered to the subject by local administration, for example by local administration to the lungs.

In some embodiments, the treatment consists of a hormonotherapy. The term "hormonotherapy" as used herein refers to slow down the growth and spread of the diseased cells in certain cases of breast cancer, by modifying in the patient's body the level of hormones linked to the disease, namely estrogen and progesterone.

The methods of reducing the level of these hormones through hormonotherapy consist of anti-estrogen drugs, also called selective estrogen receptor modulators or SERMs, block estrogen receptors by binding directly to them, thus preventing the cancer cells from obtaining estrogen. Tamoxifen (Nolvadex, Tamofen), that is available in pill form, is the most frequently used anti-estrogen drug. As for fulvestrant (Faslodex), it reduces the number of estrogen receptors on breast cancer cells. It is injected into the muscle of the buttocks. The methods also consist of the use of aromatase inhibitors, an enzyme that contributes to the body's production of estrogen. These inhibitors are also medication. However they stop the production or block the action of aromatase. They are prescribed only to menopausal women; As used herein, the terms "combined treatment", "combined therapy" or "therapy combination" refer to a treatment that uses more than one medication. The combined therapy may be dual therapy or bi-therapy.

As used herein, the term "administration simultaneously" refers to administration of 2 active ingredients by the same route and at the same time or at substantially the same time. The term "administration separately" refers to an administration of 2 active ingredients at the same time or at substantially the same time by different routes. The term "administration sequentially" refers to an administration of 2 active ingredients at different times, the administration route being identical or different.

In a particular embodiment, the invention relates to a i) radiotherapeutic agent and ii) an immunotherapeutic agent for simultaneous, separate or sequential use in the treatment of breast cancer (e.g TNBC or luminal BC subtypes).

In a particular embodiment, the invention relates to a i) chemotherapeutic agent and ii) an immunotherapeutic agent for simultaneous, separate or sequential use in the treatment of breast cancer (e.g TNBC or luminal BC subtypes).

In a particular embodiment, the invention relates to a i) radiotherapeutic agent and ii) a chemotherapeutic agent for simultaneous, separate or sequential use in the treatment of breast cancer (e.g TNBC or luminal BC subtypes).

In a particular embodiment, the invention relates to a i) radiotherapeutic agent and ii) hormonotherapy for simultaneous, separate or sequential use in the treatment of breast cancer (e.g TNBC or luminal BC subtypes).

In a particular embodiment, the invention relates to a i) chemotherapeutic agent and ii) hormonotherapy for simultaneous, separate or sequential use in the treatment of breast cancer (e.g TNBC or luminal BC subtypes).

In a particular embodiment, the invention relates to a i) an immunotherapeutic agent and ii) hormonotherapy for simultaneous, separate or sequential use in the treatment of breast cancer (e.g TNBC or luminal BC subtypes).

In some embodiments, the subject will be treated with a radiotherapeutic agent in combination with an immunotherapeutic agent if the expression level of LINC01087 is lower than its predetermined reference value.

In some embodiments, the subject will be treated with a radiotherapeutic agent in combination with a chemotherapeutic agent if the expression level of LINC01087 is lower than its predetermined reference value.

In some embodiments, the subject will be treated with an immunotherapeutic agent in combination with a chemotherapeutic agent if the expression level of LINC01087 is lower than its predetermined reference value.

In some embodiments, the subject will be treated with a radiotherapeutic agent in combination with hormonotherapy if the expression level of LINC01087 is lower than its predetermined reference value.

In some embodiments, the subject will be treated with a chemotherapeutic agent in combination with hormonotherapy if the expression level of LINC01087 is lower than its predetermined reference value.

In some embodiments, the subject will be treated with an immunotherapeutic agent in combination with hormonotherapy if the expression level of LINC01087 is lower than its predetermined reference value.

In some embodiments, the subject will be treated with a radiotherapeutic agent in combination with an immunotherapeutic agent if the expression level of LINC01087 is higher than its predetermined reference value.

In some embodiments, the subject will be treated with a radiotherapeutic agent in combination with a chemotherapeutic agent if the expression level of LINC01087 is higher than its predetermined reference value.

In some embodiments, the subject will be treated with an immunotherapeutic agent in combination with a chemotherapeutic agent if the expression level of LINC01087 is higher than its predetermined reference value.

In some embodiments, the subject will be treated with a radiotherapeutic agent in combination with hormonotherapy if the expression level of LINC01087 is higher than its predetermined reference value.

In some embodiments, the subject will be treated with a chemotherapeutic agent in combination with hormonotherapy if the expression level of LINC01087 is higher than its predetermined reference value.

In some embodiments, the subject will be treated with an immunotherapeutic agent in combination with hormonotherapy if the expression level of LINC01087 is lower than its predetermined reference value.

A "therapeutically effective amount" refers to an amount effective, at dosages and for periods of time necessary, to achieve a desired therapeutic result. A therapeutically effective amount of drug may vary according to factors such as the disease state, age, sex, and weight of the individual, and the ability of drug to elicit a desired response in the individual. A therapeutically effective amount is also one in which any toxic or detrimental effects of the antibody or antibody portion are outweighed by the therapeutically beneficial effects. The efficient dosages and dosage regimens for drug depend on the disease or condition to be treated and may be determined by the persons skilled in the art. A physician having ordinary skill in the art may readily determine and prescribe the effective amount of the pharmaceutical composition required. For example, the physician could start doses of drug employed in the pharmaceutical composition at levels lower than that required in order to achieve the desired therapeutic effect and gradually increase the dosage until the desired effect is achieved. In general, a suitable dose of a composition of the present invention will be that amount of the compound which is the lowest dose effective to produce a therapeutic effect according to a particular dosage regimen. Such an effective dose will generally depend upon the factors described above. For example, a therapeutically effective amount for therapeutic use may be measured by its ability to stabilize the progression of disease. One of ordinary skill in the art would be able to determine such amounts based on such factors as the subject's size, the severity of the subject's symptoms, and the particular composition or route of administration selected. An exemplary, non-limiting range for a therapeutically effective amount of drug is about 0.1-100 mg/kg, such as about 0.1-50 mg/kg, for example about 0.1-20 mg/kg, such as about 0.1-10 mg/kg, for instance about 0.5, about such as 0.3, about 1, about 3 mg/kg, about 5 mg/kg or about 8 mg/kg. An exemplary, non-limiting range for a therapeutically effective amount of an antibody of the present invention is 0.02-100 mg/kg, such as about 0.02-30 mg/kg, such as about 0.05-10 mg/kg or 0.1-3 mg/kg, for example about 0.5-2 mg/kg. Administration may e.g. be intravenous, intramuscular, intraperitoneal, or subcutaneous, and for instance administered proximal to the site of the target. Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. In some embodiments, the efficacy of the treatment is monitored during the therapy, e.g. at predefined points in time. As non-limiting examples, treatment according to the present invention may be provided as a daily dosage of the agent of the present invention in an amount of about 0.1-100 mg/kg, such as 0.2, 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of days 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of weeks 1, 2, 3, 4, 5, 6, 7, 8, 9, 10, 11, 12, 13, 14, 15, 16, 17, 18, 19 or 20 after initiation of treatment, or any combination thereof, using single or divided doses every 24, 12, 8, 6, 4, or 2 hours, or any combination thereof.

Typically, the radiotherapeutic agent, the immunotherapeutic agent, the chemotherapeutic agent and/or hormonotherapy as described above are administered to the subject in the form of a pharmaceutical composition which comprises a pharmaceutically acceptable carrier. Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. For use in administration to a subject, the composition will be formulated for administration to the subject. The compositions of the present invention may be administered orally, parenterally, by inhalation spray, topically, rectally, nasally, buccally, vaginally or via an implanted reservoir. The compositions used herein includes subcutaneous, intravenous, intramuscular, intra-articular, intra-synovial, intrasternal, intrathecal, intrahepatic, intralesional and intracranial injection or infusion techniques. Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include, e.g., lactose. When aqueous suspensions are required for oral use, the active ingredient is combined with emulsifying and suspending agents. If desired, certain sweetening, flavoring or coloring agents may also be added. Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols. The compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. For topical applications, the compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water. Topical application for the lower intestinal tract can be effected in a rectal suppository formulation (see above) or in a suitable enema formulation. Patches may also be used. The compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. For example, an antibody present in a pharmaceutical composition of this invention can be supplied at a concentration of 10 mg/mL in either 100 mg (10 mL) or 500 mg (50 mL) single-use vials.

The product is formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. An exemplary suitable dosage range for an antibody in a pharmaceutical composition of this invention may between about 1 mg/m2 and 500 mg/m2. However, it will be appreciated that these schedules are exemplary and that an optimal schedule and regimen can be adapted taking into account the affinity and tolerability of the particular antibody in the pharmaceutical composition that must be determined in clinical trials. A pharmaceutical composition of the invention for injection (e.g., intramuscular, i.v.) could be prepared to contain sterile buffered water (e.g. 1 ml for intramuscular), and between about 1 ng to about 100 mg, e.g. about 50 ng to about 30 mg or more preferably, about 5 mg to about 25 mg, of the inhibitor of the invention.

The invention will be further illustrated by the following figures and examples. However, these examples and figures should not be interpreted in any way as limiting the scope of the present invention.

FIGURES

FIG. 1. LINC01087 is downregulated in TNBC tissues. (A) Expression of LINC01087 quantitated in breast tissue samples by RNA-Seq. (B) Expression of LINC01087 in breast tissue samples from the TCGA database. (A, B) Graphs illustrate both box plots and individual values expressed as log 2(CPM+0.5). $^{}p \leq 0.01$, $^{**}p \leq 0.0001$. CPM, count per million; Lum A, luminal A; Lum B, luminal B; TNBC, triple negative breast cancer.

FIG. 2. The expression level of LINC01087 predicts survival of breast cancer patients. Kaplan-Meier Plotter online database was used to generate the survival curves according to the level of expression of LINC01087. Kaplan-Meier analysis of RFS (A), DMFS (B) and OS (C) of breast cancer patients expressing high versus low level of LINC01087. RFS analyses for LINC01087 expression of TNBC breast cancer patients (D; n=161; *p=2e-04) and, more specifically in patients affected by a TNBC of basal intrinsic subtype (E; n=118; *p=0.00012). RFS analyses according to the expression level of LINC01087 in patients with advanced TNBC (grade 3 tumor, lymph node involvement) either without (F; n=29; p=7e-04) or with (G; n=22; *p=1e-04) basal intrinsic features. RFS analyses for LINC01087 expression of luminal A (H; n=841; **p=9.2e-07) and luminal B (I; n=407; p=0.0057) breast cancer patients. OS analysis for LINC01087 expression of luminal A breast cancer patients (J; n=271; **p=0.0019). BC, breast cancer; BLBC, basal-like breast cancer subtype; DMFS, distant metastasis-free survival; G3, grade 3 tumor; N+, positive lymph node status; OS, overall survival; RFS, relapse-free survival; TNBC, triple negative breast cancer.

FIG. 3. The deregulation of LINC01087 segregates BC molecular subtypes, regardless of the mutational status of BC. Representation of LINC01087 expression in BC patients harboring tumors with wild-type or mutant versions of the tumor suppressors TP53, BRCA1, and BRCA2. (A) Wild-type controls: WT/0,0,0=TP53wt, BRCA1wt, BRCA2wt. (B) TP53m=TP53 mutated tumors (regardless of the mutational status of BRCA1&2); BRCA1m=BRCA1 mutated (regardless of TP53 & BRCA2 mutations); BRCA2m=BRCA2 mutated (regardless of TP53 & BRCA1 mutations). (C) 0,0,1=TP53wt, BRCA1wt, BRCA2m; 0,1,0=TP53wt, BRCA1m, BRCA2wt; 1,0,0=TP53m, BRCA1wt, BRCA2wt; 1,0,1=TP53m, BRCA1wt, BRCA2m; 1,1,0=TP53m, BRCA1m, BRCA2wt. Of note, other combinations of mutations were not observed among the cohorts available. (D) LINC01087 expression in TP53m tumors subdivided according to their molecular subtype. The level of LINC01087 expression is reported as log 2(CPM+0.5) for each patient's BC samples from both TCGA and cBioPortal databases (a-c). Symbols indicate significant changes with respect to WT/0,0,0 (wild-type controls) ($^{}p \leq 0.01$, $^{**}p \leq 0.0001$), or to TP53m ($\$ \leq 0.05$), or to BRCA2m ($\# \leq 0.05$), or to 0,0,1 (TP53wt, BRCA1wt, BRCA2m) ($\& \leq 0.05$) samples. BC, breast cancer; CPM, counts per million; TNBC, triple negative breast cancer.

EXAMPLE

Material & Methods

Patient Samples

Sixty-one breast tissue specimens (16 paired adjacent non-tumor tissues, 17 luminal A, 9 luminal B, 4 HER2+ and 15 TNBC breast tumor samples) were collected from cancer patients attending the Senology Department of the "Istituto Nazionale dei Tumori—Fondazione G. Pascale" of Naples, Italy. All breast tissues were snap-frozen in liquid nitrogen after surgery and cryopreserved at −80° until used. Histological and molecular tests were performed to evaluate the immunoprofile of each breast tissue. All patients provided their written informed consent for the research purpose of these clinical materials according to the tenets of the Helsinki Declaration. This study was approved by the Istituto Nazionale Tumori—Fondazione G. Pascale Ethics Committee (protocol number 3 of Mar. 25, 2009).

Laser-Capture Microdissection

Human breast tissue samples were all subjected to laser-capture microdissection (LCM). Frozen sections of each tissue sample were embedded in Optimal Cutting Temperature (OCT) compound, cut at 14 μm thickness and placed on polyethylene sulfide (PPS) membrane slides (Microdissect GmbH, Herborn, Germany). Then, all PPS slides were fixed in 70% ethanol for 1 minute, haematoxylin and eosin stained for 30 seconds, followed by three dehydration steps in 90%, 95% and 99% ethanol for 1 minute each, and air-dried. Finally, about 10 to 20 million $\mu m^2$ of microdissected tissue was obtained from each stained sample using Leica LMD6000 microdissection system (Wetzlar, Germany), according to the manufacturer's instructions.

Bioinformatic and Statistical Analyses

For in silico analyses, data of BC patients from the Cancer Genome Atlas (TCGA) were downloaded from the website Genomic Data Commons (https://portal.gdc.cancer.gov). The analysis of differential lncRNAs expression was performed using limma R/Biodonductor. A gene was determined as significantly differentially expressed when its associated empirical Bayes moderated t-p-value corrected by Benjamini-Hochberg procedure was ≤0.05. The edgeR R/Biodonductor package was used to normalize RNAseq data considering only lncRNAs.

Wilcoxon rank-sum tests were used to assess the statistical significance of the difference of expression of LINC01087 regarding BRCA1 and TP53 mutational status in BC patients.

To test the role of LINC01087 as a biomarker of BC prognosis, survival curves were plotted using the online survival analysis tool, namely "Kaplan-Meier Plotter" (http://kmplot.com/analysis/). Best cutoff and probe set options were selected for the survival curves analyses.

Results

LINC01087 is Downregulated in TNBC and Upregulated in Luminal Breast Tissues

To identify a lncRNA signature in BC, and particularly in the TNBC subtype, and to examine the role of a dysregulated expression of lncRNAs in breast carcinogenesis, we applied two complementary approaches.

First, we investigated the expression profile of lncRNAs in 60 laser-microdissected breast tissues by high-throughput sequencing of rRNA-depleted RNA method. Second, available TCGA data from 813 samples (113 normal, 427 luminal A, 121 luminal B, 37 HER2+ and 115 TNBC patients) were screened for differential expression of lncRNAs in silico.

Among the list of lncRNAs significantly modulated in our cohort of BC patients, LINC01087 exhibited decreased expression specifically in TNBCs as compared to normal breast tissues, as well as to luminal A and B tissues (FIG. 1A). Moreover, the interrogation of the TCGA database confirmed that LINC01087 is down-regulated in TNBCs compared to normal and luminal breast tissues (FIG. 1B). Additionally, LINC01087 exhibited increased expression specifically in luminal BCs as compared to normal breast tissues, as well as to TNBC tissues (FIG. 1A). Moreover, the interrogation of the TCGA database confirmed that LINC01087 is up-regulated in luminal BCs compared to normal and TNBC tissues (FIG. 1B).

Altogether, these data confirmed that LINC01087 was significantly downregulated in TNBC and upregulated in luminal BCs.

LINC01087 Downregulation is Associated with Poor Relapse-Free Survival in TNBC

The relationship between LINC01087 downregulation and survival of BC patients has been explored. We used publicly available data of breast cancer patients from the Kaplan-Meier plotter (KMplot) platform (kmplot.com). The effect of the down-expression of LINC01087 was explored in different datasets and particularly on relapse-free survival (RFS) and, when the number of samples available in the database was sufficient, on distant metastasis-free survival (DMFS) and overall survival (OS).

Figures 2A, 2B:
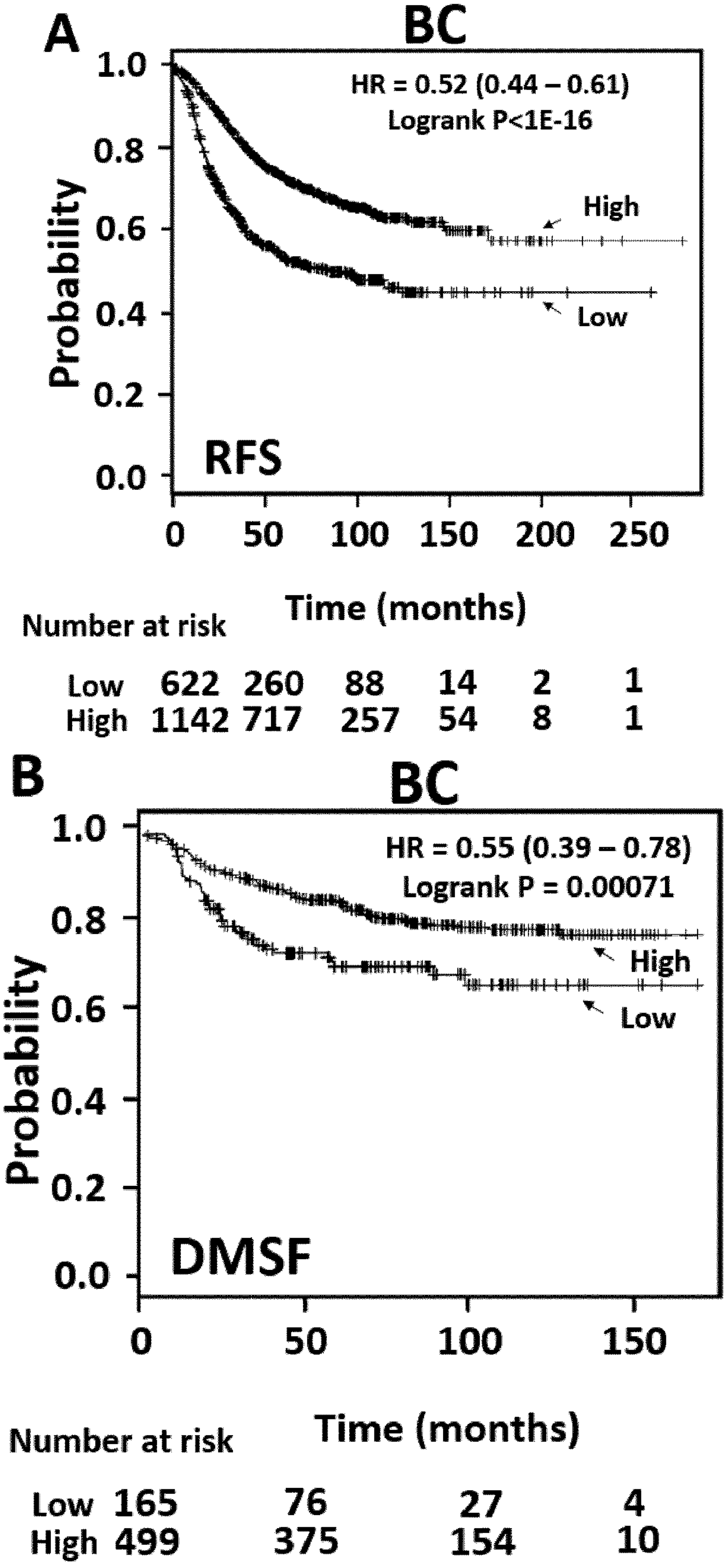
Figure 2C:
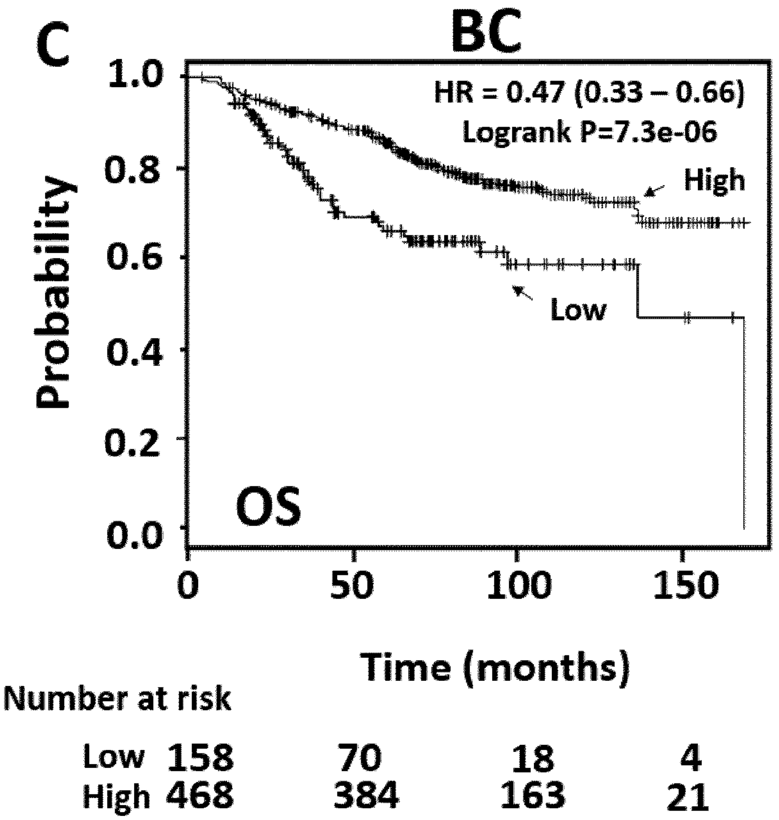

In a first analysis comprising BC tissues without further consideration of their subtype classification, patients presenting a reduced expression of LINC01087 in BC samples exhibited lower RFS (n=1764; p≤1e-16), DMSF (n=664; p=0.0007) and OS (n=626; p=7.3e-06) (FIG. 2A-C). Overall, low expression of LINC01087 correlated with poorer clinical outcome.

Furthermore, the Kaplan-Meier plotter web-tool allows to filter BC patients according to the receptor and lymph node status, histological grade, type of treatment as well as tumor intrinsic subtype. The latter is defined based on immunohistochemical markers (ER, PR and HER2) and can be further sub-classified according to gene expression patterns.

Figure 2D:
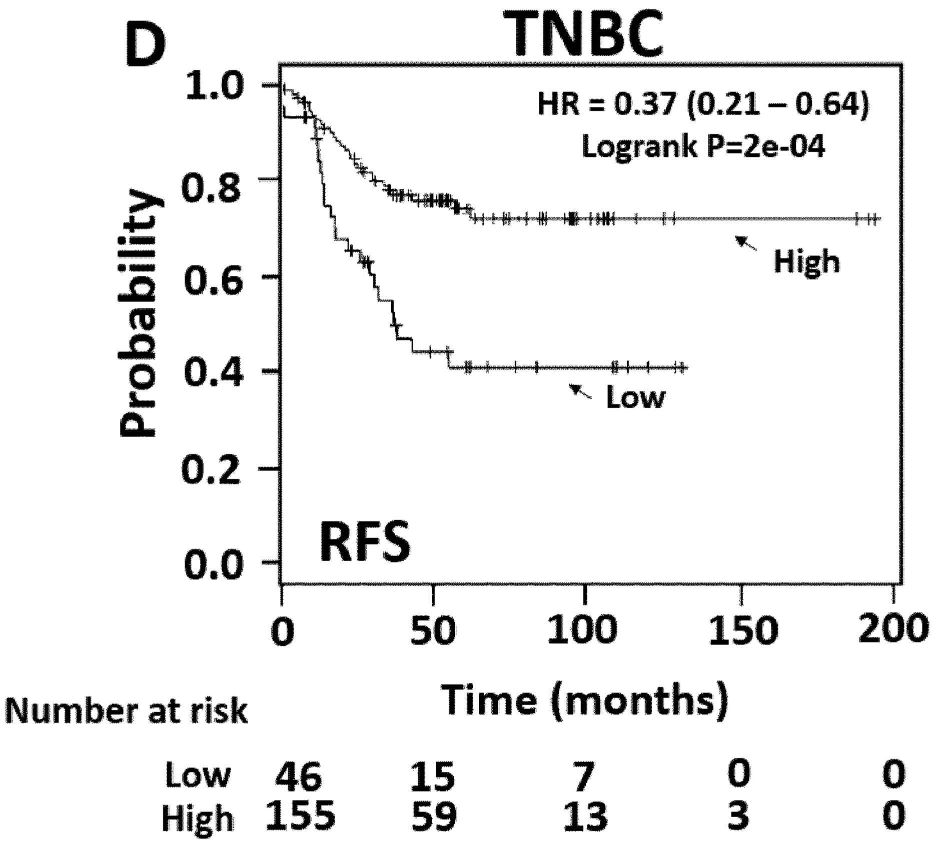
Figure 2E:
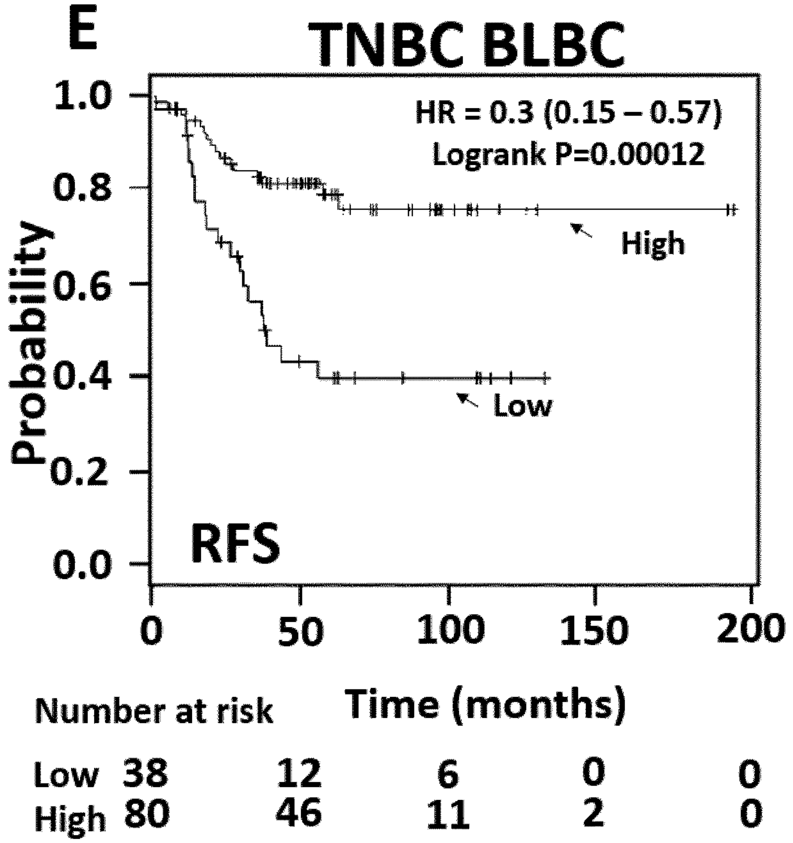

In this line, we restricted LINC01087-related RFS analyses to TNBC cases, defined as ER−, PR− and HER2− patients (FIG. 2D). In addition, we analyzed LINC01087-related RFS in TNBC patients of the basal-like breast cancer (BLBC) subtype (FIG. 2E). The BLBC subtype is defined by a cluster of genes expressed in the basal or outer layer of the mammary gland epithelium. It accounts for about 60-90% of TNBCs and is characterized by an aggressive clinical course and resistance to targeted therapies[28]. Low expression of LINC01087 correlated with poorer RFS in TNBC patients (n=161; p=2e-04), including the most prevalent subtype, BLBC (n=118; p=0.00012) (FIG. 2D, 2E).

Figure 2F:
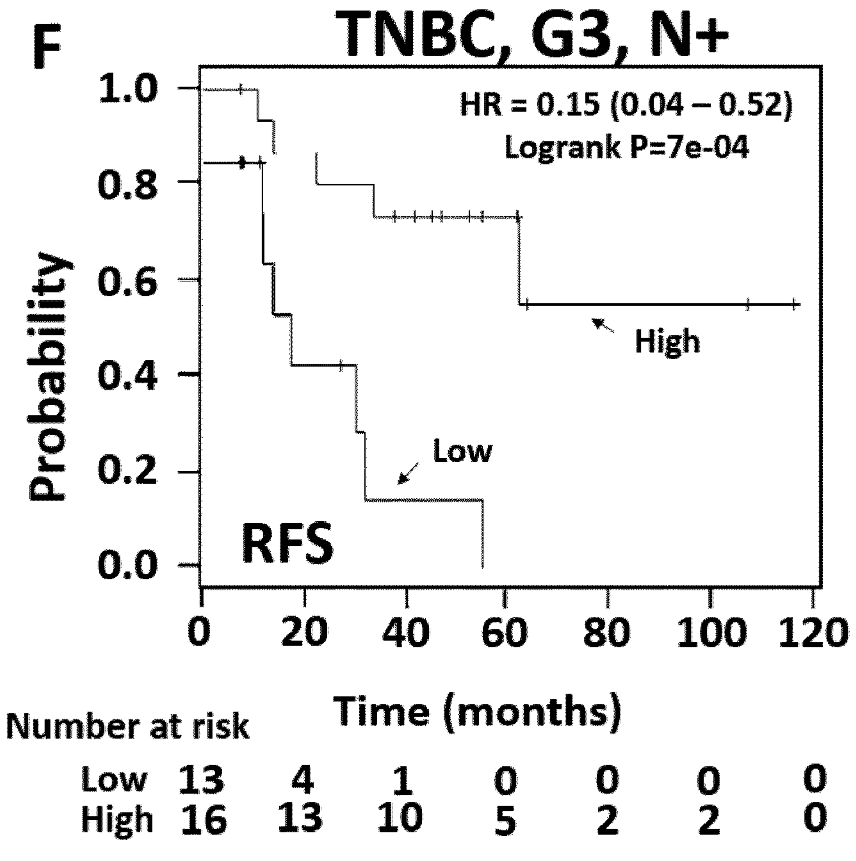
Figure 2G:
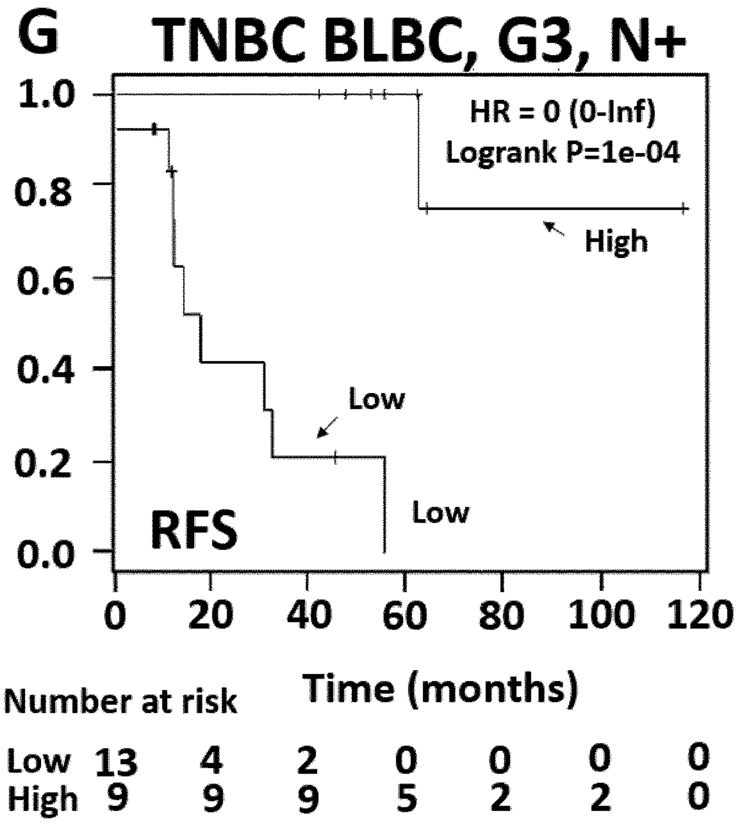

Current routine clinical management of breast cancer is also based on the evaluation of the histological tumor grade and nodal involvement. These two parameters are widely recognized as markers of aggressiveness and are related to a poorer prognosis in BC patients[29, 30, 31]. To strengthen the prognostic role of a down-expression of LINC01087 in TNBCs, we evaluated the RFS of patients diagnosed with advanced TNBC (i.e. positive lymph node status [N+] and grade 3 [G3] tumor), harboring or not basal-like features (FIG. 2F, 2G). In these aggressive TNBCs, the expression level of LINC01087 was remarkably prognosing patient outcome, independently of the BLBC sub-classification. Indeed, worsen RFS were observed in TNBC patients whose tumor expressed low levels of the LINC (n=29; p=7e-04), including the most prevalent subtype, BLBC (n=22; p=1e-04) (FIG. 2D, 2E).

Altogether, these multivariate analyses of Kaplan-Meier survival curves evidenced an association between a low expression of LINC01087 and a worsen outcome in all selected cohorts, particularly of the TNBC subtype. Therefore, the expression level of LINC01087 could be considered as a prognosis biomarker in TNBC.

LINC01087 Upregulation is Associated with Better Relapse-Free Survival in Luminal Breast Cancers Similarly to TNBC, the relationship between LINC01087 upregulation and the survival of luminal patients has been explored using KMplot. The effect of the over-expression of LINC01087 was explored in different datasets and particularly on relapse-free survival (RFS) and overall survival (OS).

Figure 2H:
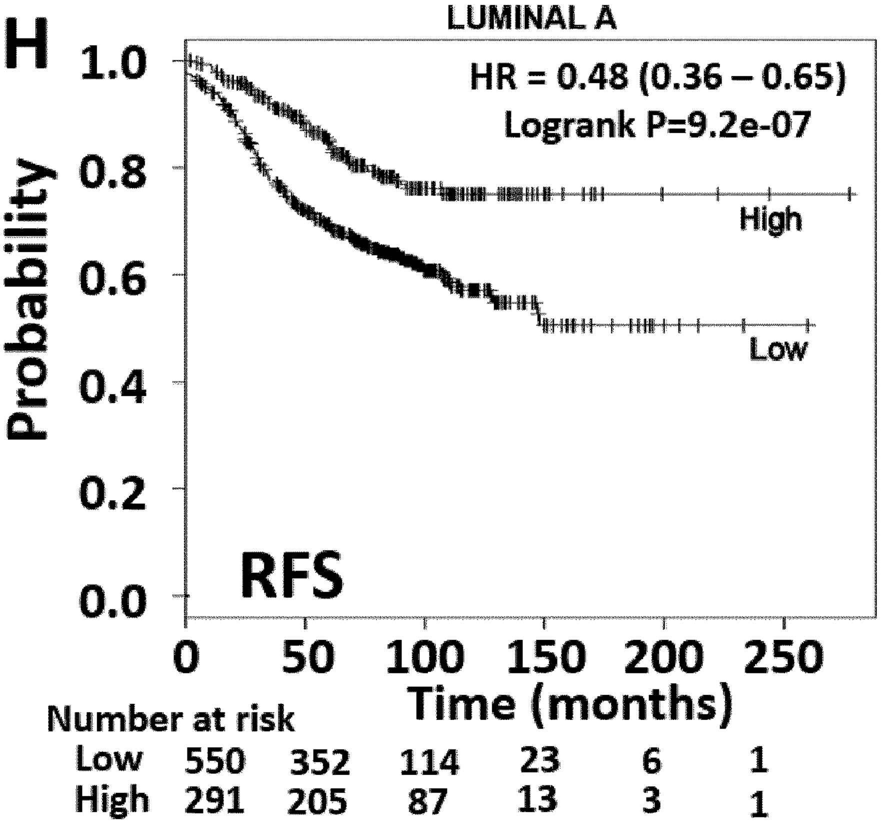
Figure 2I:
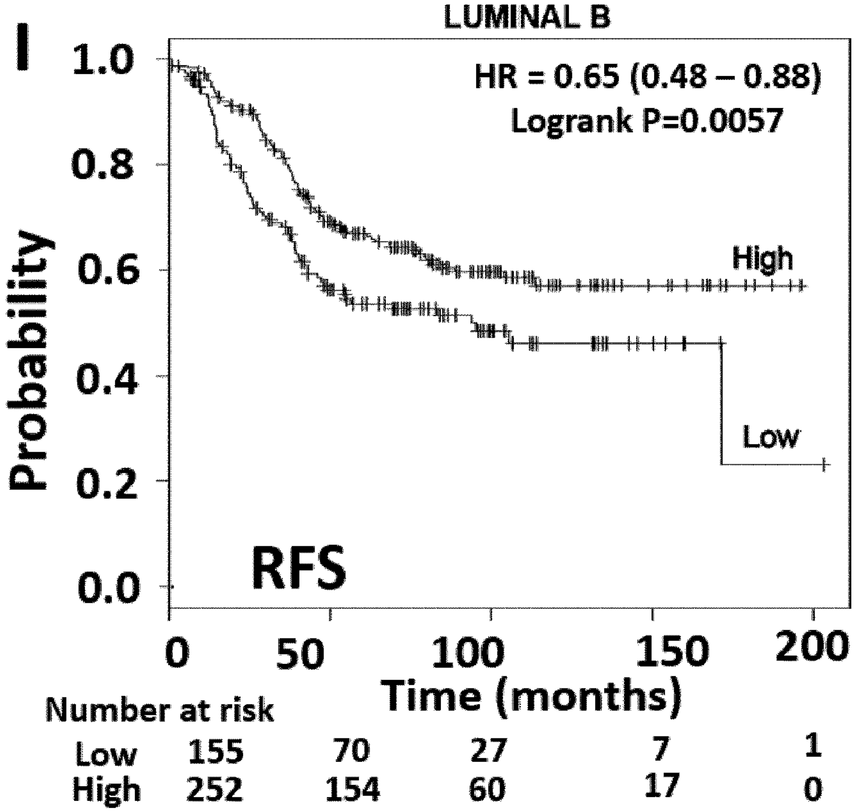
Figure 2J:
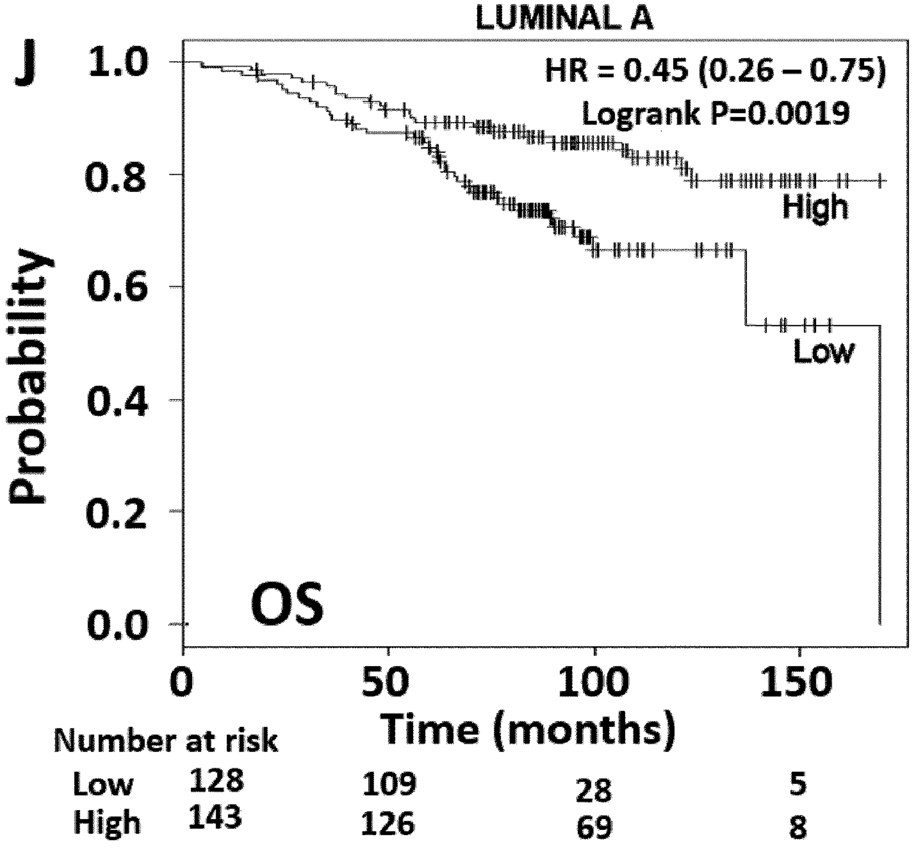

High expression of LINC01087 correlated with extended RFS in patients affected with luminal A (n=841; p=9.2e-07) and luminal B (n=407; p=0.0057) breast cancers (FIG. 2H, 2I). Similarly, an extended OS was witnessed in luminal A BCs expressing a high level of LINC01087 (n=271; p=0.0019) (FIG. 2J).

Thus, these multivariate analyses of Kaplan-Meier survival curves evidenced an association between a high expression of LINC01087 and a better outcome in the luminal subtypes. Therefore, the expression level of LINC01087 could be considered as a prognosis biomarker in luminal patients.

LINC01087 Deregulation is Associated with Molecular Subtypes, Independently of the Histological and Mutational Status of Breast Cancer To determine whether the modulated expression of LINC01087 could contribute to the development and/or progression of breast cancer, we investigated its association with common clinical parameters and histological origin of the tumor within the cohort of BC patients available in the TCGA database.

At first sight, the expression of LINC01087 appeared differentially regulated across the different histological subtypes of breast tumors. Indeed, it was less abundant in aggressive and invasive metaplastic carcinomas as compared to infiltrating ductal carcinomas or lobular carcinomas (data not shown). However, by subdividing the most represented histological subtype (i.e. infiltrating ductal carcinoma), according to its molecular features (luminal A, B or TNBC), we noticed a predominant association between the downregulation of LINC01087 and the TNBC molecular subtype, independently of the histological nature of BC (data not shown).

In parallel, LINC01087 was more abundantly expressed in lobular carcinoma (data not shown). However, by subdividing this histological subtype according to its molecular features (luminal A, B or TNBC), we noticed an overrepresentation of the luminal subtypes. Thus, the upregulation of LINC01087 appeared associated with the luminal molecular subtype, independently of the histological nature of BC (data not shown).

Moreover, regarding the clinicopathological characteristics (e.g. age, gender, tumor stage and size), the size of the tumor appeared significantly associated with LINC01087 expression in the TCGA analysis (data not shown).

Next, we investigated if the dysregulated expression of LINC01087 could be a prognostic indicator of BC aggressiveness. Considering the important role played by the detection test of BRCA1/2 gene mutations in assessing the risk of BC development, prognosis prediction and therapy responsiveness, we analyzed the possibility that LINC01087 expression might vary depending on the mutational status of BRCA1/2[32, 33]. Moreover, approximately 30% of BCs present a mutation in the gene TP53[34]. These TP53 mutations have a negative prognostic value and are associated with an aggressive phenotype, such as TNBC, as well as with chemoresistance[35].

Therefore, we compared the expression of LINC01087 in BC patient samples harboring mutations in three major tumor suppressors BRCA1 (BRCA1m), BRCA2 (BRCA2m) or TP53 (TP53m) with a control arm carrying wild-type copies of these genes (BRCA1wt, BRCA2wt, TP53wt). This latter analysis revealed a significantly reduced expression of LINC01087 in BC patients bearing BRCA1 and TP53 mutated tumors in comparison to wild-type samples. In contrast, no significant differences were observed for BRCA2 (FIG. 3A, 3B).

Figures 3A, 3B, 3C:
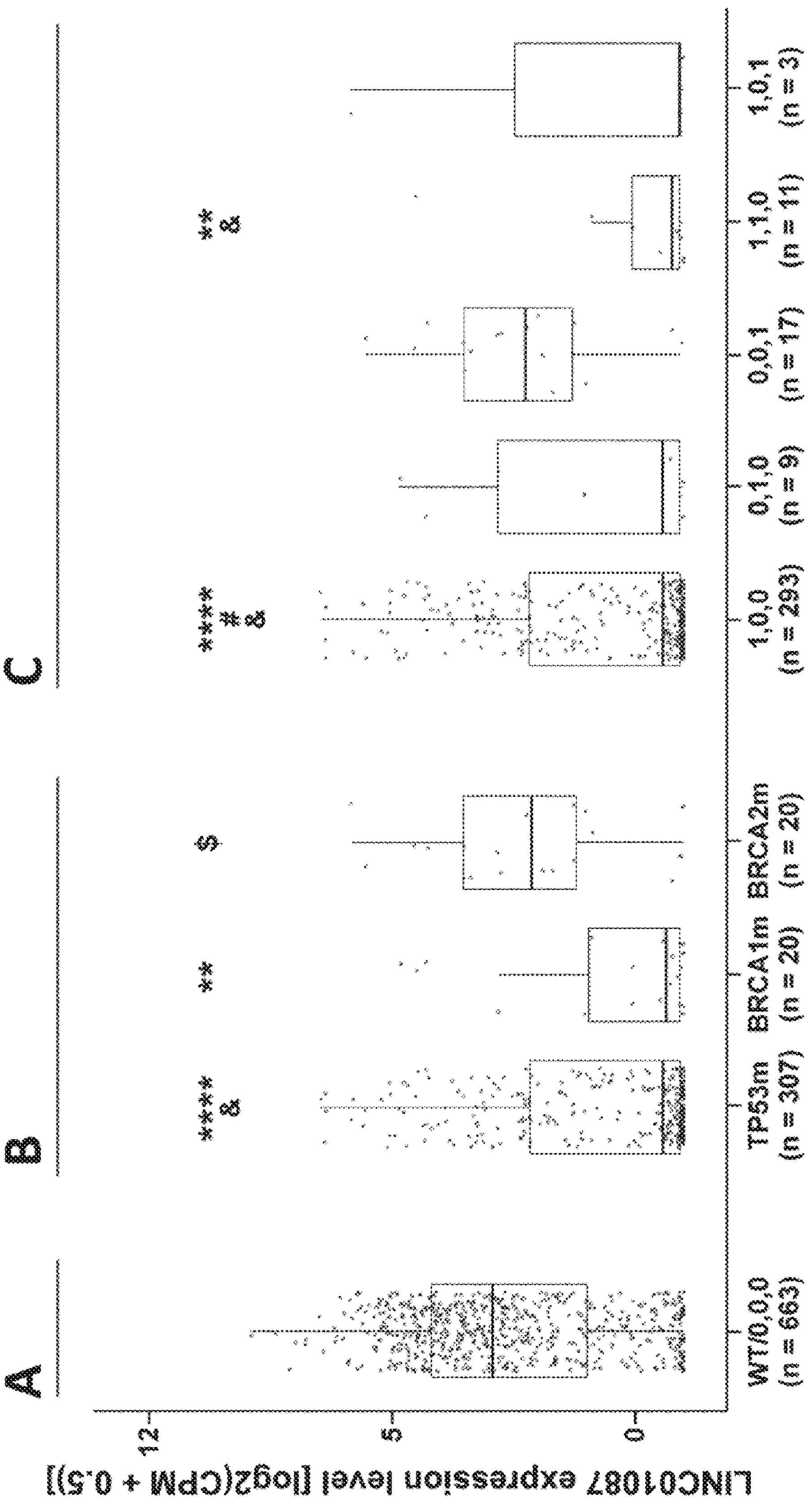

To refine our analysis, we investigated the expression level of LINC01087 according to the mutational status of all three genes, rather than one single, at a time (FIG. 3C). In comparison to wild-type BC samples, the expression of LINC01087 was effectively weaker in BC patients bearing mutations of TP53, regardless of the BRCA1 mutational status. In the absence of mutated TP53, neither BRCA1 nor BRCA2 mutations were associated with an aberrant expression of LINC01087 (FIG. 3C).

Figure 3D:
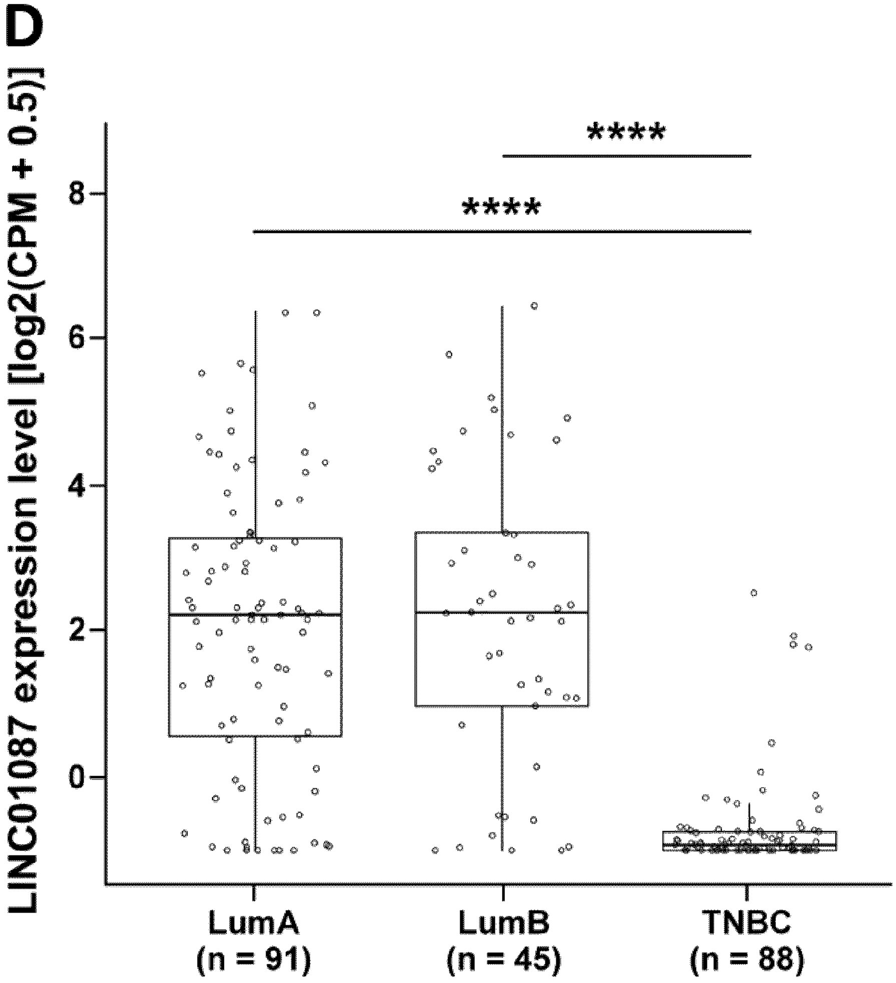

In the next step, we aimed at weighing the importance of the mutational status over the molecular subtype of BC on the regulation of LINC01087 expression. As we did for the histological data, when the information was available, we subdivided the largest cohort of patients with mutated tumor suppressors, i.e. BCs with a single mutation in TP53 (FIG. 3C), based on their molecular features. Once again, within TP53m BC samples, LINC01087 was barely expressed in TNBC, whereas its level was higher in the luminal A and B subtypes (FIG. 3D). Thus, despite the presence of mutations in genes affiliated with tumor aggressiveness, the level of LINC01087 expression was still segregating TNBC from luminal cancers.

In conclusion, these findings highlight the potential value of LINC01087 downregulation for diagnosing the TNBC and of its upregulation for the luminal molecular subtypes, regardless of the clinicopathological parameters, histological nature and TP53/BRCA1/2 mutational status of BC.

Discussion

Considering the aggressiveness of the TNBC subtype and its negative impact on the therapeutic response, clinical outcomes and survival rate[5,10] there is an urgent need for identifying specific biomarkers allowing for its early diagnosis and prognostic stratification.

In the last decade, cumulative studies emphasized the functional relevance of lncRNAs in breast cancer and proposed their consideration to classify the heterogeneous collection of BC subtypes[20, 22, 41]. These findings have provided in-depth knowledge of the regulatory mechanisms that drive breast tumorigenesis[36]. In the routine clinical research and practice, the perturbation of lncRNAs expression has raised consideration for improving the care of TNBC. Therefore, we first applied a high-throughput sequencing approach, followed by bioinformatics analyses in order to define a specific signature of lncRNAs in the TNBC subtype. Among all the lncRNAs identified, we focused our attention on a strongly modulated intergenic lncRNA named LINC01087, which has been under-investigated so far.

In this study, we described a deregulated expression of LINC01087 as a diagnostic and prognostic biomarker for TNBC and luminal BCs. In both RNA-sequencing and bioinformatics analyses, LINC01087 was weakly expressed in TNBC patient samples and highly expressed in luminal samples as opposed to normal specimens. Such differential expression between TNBC and luminal subtypes has been validated in vitro in breast cancer cell lines.

The clinical behavior of TNBCs remains difficult to predict. Generally, TNBCs have the worst clinical outcome and highest rate of recurrence within the first 5-years that follow diagnosis[7, 8]. Efforts are being made to identify some biomarkers that could stratify patients into subgroups with low versus high risk of recurrence and short- versus long-term survival. Thus, the potential prognostic value of LINC01087 was studied using the Kaplan-Meier plotter online database. The survival curves showed that a down-expression of LINC01087 was substantially correlated with a lower RFS in TNBC patients, especially in advanced stages characterized by a lymph node involvement and a high-grade tumor. Thus, quantitative detection of LINC01087 may be clinically useful for the diagnosis of the TNBC subtype and its gradation and, consequently, as a prognostic biomarker in TNBC patients.

Luminal BCs have a better prognosis. Still, identifying novel biomarkers with enhanced diagnostic and prognostic value may improve therapeutic management and positively impact disease outcome. Following interrogation of the KMplot database, we reported that high level of LINC01087 correlated with extended RFS in both luminal A and B cohorts, as well as prolonged OS in luminal A patients. Thus, quantitative detection of LINC01087 may be clinically useful for the diagnosis and prognosis of the luminal subtypes.

BC is a complex genetic disease that demonstrates a high prevalence of TP53 mutations, particularly in TNBCs[43]. Detection of alterations in TP53 is considered a negative prognostic factor due to its association with more aggressive BC subtypes when compared to BC subjects who possess wild-type copies of TP53[44]. In addition, BC patients that harbor TP53 mutations can carry alterations in the genes BRCA1/BRCA2, thus increasing cancer aggressiveness[45]. Therefore, to evaluate the impact of LINC01087 on BC prognosis, we measured its level of expression according to the mutational status of BRCA1 and BRCA2, as well as to that of TP53. Interestingly, we noticed a significant decrease of LINC01087 in TP53-mutated specimens, regardless of BRCA1/2 mutational status. Nevertheless, these correlations ultimately depended on the TNBC molecular subtype, which is naturally enriched in the samples mutated for TP53. Moreover, within TP53 mutated BC patients, tumor samples with high level of LINC01087 corresponded to luminal BCs. Altogether, these results demonstrate that the expression level of LINC01087 can determine the molecular subtype of BC, independently of its mutational status.

Prospective clinical studies gathering a larger number of patients and covering the different clinicopathological, histological and mutational subtypes of BC must consolidate our findings on the diagnostic and prognostic value of a downregulated LINC01087 in TNBC and its upregulation in luminal BCs.

In the scenario of a potential role of LINC01087 in breast carcinogenesis and cancer aggressiveness, we initiated some investigations to characterize the biological processes in which LINC01087 could be involved in TNBC. First, an in silico comparative analysis between TNBC samples harboring low versus intermediate level of LINC01087, revealed 43 genes whose expression positively correlated with LINC01087 expression. Bioinformatics analyses and in vitro assays showed that these LINC01087-related genes were mostly involved in cell proliferation and survival, as well as chemo-resistance (data not shown).

In summary, LINC01087 is a new intergenic lncRNA involved in breast carcinogenesis. Detection of its down-regulation represents a new potential biomarker for the diagnosis and prognosis of TNBC patients, while its upregulation could be exploited for the diagnosis and prognosis of luminal patients. Such diagnostic and prognostic values may contribute to improve treatment management of BCs. Further investigations will be needed to identify and validate the molecular targets/interactors of LINC01087. Such basic knowledge could ultimately be exploited for the design of novel targeted therapies.

REFERENCES

Throughout this application, various references describe the state of the art to which this invention pertains. The disclosures of these references are hereby incorporated by reference into the present disclosure.

1 Molecular evolution of breast cancer—Simpson—2005—The Journal of Pathology—Wiley Online Library. https://onlinelibrary.wiley.com/doi/full/10.1002/path.1691 (accessed 24 May 2019).

2 Russnes H G, Lingjoxrde O C, Borresen-Dale A-L, Caldas C. Breast Cancer Molecular Stratification. Am J Pathol 2017; 187: 2152-2162.

3 Rakha E A, Green A R. Molecular classification of breast cancer: what the pathologist needs to know. Pathology (Phila) 2017; 49: 111-119.

4 Lehmann B D, Bauer J A, Chen X, Sanders M E, Chakravarthy A B, Shyr Y et al. Identification of human triple-negative breast cancer subtypes and preclinical models for selection of targeted therapies. J Clin Invest 2011; 121: 2750-2767.

5 Pareja F, Reis-Filho J S. Triple-negative breast cancers—a panoply of cancer types. Nat. Rev. Clin. Oncol. 2018. doi:10.1038/s41571-018-0001-7.

6 Nedeljković M, Damjanović A. Mechanisms of Chemotherapy Resistance in Triple-Negative Breast Cancer—How We Can Rise to the Challenge. Cells 2019; 8: 957.

7 Bianchini G, Balko J M, Mayer I A, Sanders M E, Gianni L. Triple-negative breast cancer: challenges and opportunities of a heterogeneous disease. Nat Rev Clin Oncol 2016; 13:674-690.

8 Dent R, Trudeau M, Pritchard K I, Hanna W M, Kahn H K, Sawka C A et al. Triple-Negative Breast Cancer: Clinical Features and Patterns of Recurrence. Clin Cancer Res 2007; 13: 4429-4434.

9 Duffy M J, Harbeck N, Nap M, Molina R, Nicolini A, Senkus E et al. Clinical use of biomarkers in breast cancer: Updated guidelines from the European Group on Tumor Markers (EGTM). Eur J Cancer 2017; 75: 284-298.

10 Inoue K, Fry E A. Novel Molecular Markers for Breast Cancer. Biomark Cancer 2016; 8: 25-42.

11 Ludwig J A, Weinstein I N. Biomarkers in Cancer Staging, Prognosis and Treatment Selection. Nat Rev Cancer 2005; 5: 845.

12 Chiu A M, Mitra M, Boymoushakian L, Coller H A. Integrative analysis of the inter-tumoral heterogeneity of triple-negative breast cancer. Sci Rep 2018; 8: 11807.

13 Tian T, Wang M, Lin S, Guo Y, Dai Z, Liu K et al. The Impact of lncRNA Dysregulation on Clinicopathology and Survival of Breast Cancer: A Systematic Review and Meta-analysis. Mol Ther—Nucleic Acids 2018; 12: 359-369.

14 Huarte M. The emerging role of lncRNAs in cancer. Nat Med 2015; 21: 1253-1261.

15 DiStefano J K. The Emerging Role of Long Noncoding RNAs in Human Disease. Methods Mol Biol Clifton NJ 2018; 1706: 91-110.

16 Di Cecilia S, Zhang F, Sancho A, Li S D, Aguilo F, Sun Y et al. RBM5-AS1 is critical for self-renewal of colon cancer stem-like cells. Cancer Res 2016; 76: 5615-5627.

17 Dhanoa J K, Sethi R S, Verma R, Arora J S, Mukhopadhyay C S. Long non-coding RNA: its evolutionary relics and biological implications in mammals: a review. J Anim Sci Technol 2018; 60. doi:10.1186/s40781-018-0183-7.

18 Ponting C P, Oliver P L, Reik W. Evolution and Functions of Long Noncoding RNAs. Cell 2009; 136: 629-641.

19 Cheetham S W, Gruhl F, Mattick J S, Dinger M E. Long noncoding RNAs and the genetics of cancer. Br J Cancer 2013; 108: 2419-2425.

20 Mathias C, Zambalde E P, Rask P, Gradia D F, Oliveira J C de. Long non-coding RNAs differential expression in breast cancer subtypes: What do we know? Clin Genet 2019; 95: 558-568.

21 Shin V Y, Chen J, Cheuk I W-Y, Siu M-T, Ho C-W, Wang X et al. Long non-coding RNA NEAT1 confers oncogenic role in triple-negative breast cancer through modulating chemoresistance and cancer sternness. Cell Death Dis 2019; 10. doi:10.1038/s41419-019-1513-5.

22 Tian T, Gong Z, Wang M, Hao R, Lin S, Liu K et al. Identification of long non-coding RNA signatures in triple-negative breast cancer. Cancer Cell Int 2018; 18. doi:10.1186/s12935-018-0598-8.

23 Han Y J, Boatman S M, Zhang J, Du X C, Yeh A C, Zheng Y et al. LncRNA BLAT1 is Upregulated in Basal-like Breast Cancer through Epigenetic Modifications. Sci Rep 2018; 8: 15572.

24 Wang S, Ke H, Zhang H, Ma Y, Ao L, Zou L et al. LncRNA MIR100HG promotes cell proliferation in triple-negative breast cancer through triplex formation with p27 loci. Cell Death Dis 2018; 9: 805.

25 Yang F, Lv S-X, Lv L, Liu Y-H, Dong S-Y, Yao Z-H et al. Identification of lncRNA<em> FAM83H-AS1</em> as a novel prognostic marker in luminal subtype breast cancer. OncoTargets Ther. 2016. doi:10.2147/OTT.S110055.

26 Zhang L, Song X, Wang X, Xie Y, Wang Z, Xu Y et al. Circulating DNA of HOTAIR in serum is a novel biomarker for breast cancer. Breast Cancer Res Treat 2015; 152: 199-208.

27 Wang P-S, Chou C-H, Lin C-H, Yao Y-C, Cheng H-C, Li H-Y et al. A novel long non-coding RNA linc-ZNF469-3 promotes lung metastasis through miR-574-5p-ZEB1 axis in triple negative breast cancer. Oncogene 2018; 37: 4662.

28 Rakha E A, Ellis I O. Triple-negative/basal-like breast cancer: review. Pathology (Phila) 2009; 41: 40-47.

29 Rakha E A, Reis-Filho J S, Baehner F, Dabbs D J, Decker T, Eusebi V et al. Breast cancer prognostic classification in the molecular era: the role of histological grade. Breast Cancer Res BCR 2010; 12: 207.
30 Simpson J F, Gray R, Dressler L G, Cobau C D, Falkson C I, Gilchrist K W et al. Prognostic value of histologic grade and proliferative activity in axillary node-positive breast cancer: results from the Eastern Cooperative Oncology Group Companion Study, EST 4189. J Clin Oncol Off J Am Soc Clin Oncol 2000; 18: 2059-2069.
31 Zheng K, Tan J-X, Li F, Li H-Y, Zeng X-H, Ma B-L et al. Clinicopathologic Factors Related to the Histological Tumor Grade of Breast Cancer in Western China: An Epidemiological Multicenter Study of 8619 Female Patients. Transl Oncol 2018; 11: 1023-1033.
32 Wallace A J. New challenges for BRCA testing: a view from the diagnostic laboratory. Eur J Hum Genet 2016; 24: S10-S18.
33 Tung N M, Garber J E. BRCA 1/2 testing: therapeutic implications for breast cancer management. Br J Cancer 2018; 119: 141-152.
34 Ungerleider N A, Rao S G, Shahbandi A, Yee D, Niu T, Frey W D et al. Breast cancer survival predicted by TP53 mutation status differs markedly depending on treatment. Breast Cancer Res 2018; 20: 115.
35 Huszno J, Grzybowska E. TP53 mutations and SNPs as prognostic and predictive factors in patients with breast cancer. Oncol Lett 2018; 16: 34-40.
36 Liu Y, Sharma S, Watabe K. Roles of lncRNA in breast cancer. Front Biosci Sch Ed 2015; 7: 94-108.
37 Kikuchi Y, Umemura H, Nishitani S, Iida S, Fukasawa R, Hayashi H et al. Human mediator MED17 subunit plays essential roles in gene regulation by associating with the transcription and DNA repair machineries. Genes Cells Devoted Mol Cell Mech 2015; 20: 191-202.
38 Ceccaldi R, Rondinelli B, D'Andrea A D. Repair Pathway Choices and Consequences at the Double-Strand Break. Trends Cell Biol 2016; 26: 52-64.
39 Branzei D, Foiani M. Regulation of DNA repair throughout the cell cycle. Nat Rev Mol Cell Biol 2008; 9: 297-308.
40 Yadav B S, Chanana P, Jhamb S. Biomarkers in triple negative breast cancer: A review. World J Clin Oncol 2015; 6: 252-263.
41 Peng J, Zhang L, Yuan C, Zhou L, Xu S, Lin Y et al. Expression profile analysis of long noncoding RNA in ER-positive subtype breast cancer using microarray technique and bioinformatics. Cancer Manag Res 2017; 9: 891-901.
42 Zhu S, Li W, Liu J, Chen C-H, Liao Q, Xu P et al. Genome-scale deletion screening of human long non-coding RNAs using a paired-guide RNA CRISPR-Cas9 library. Nat Biotechnol 2016; 34: 1279-1286.
43 Na B, Yu X, Withers T, Gilleran J, Yao M, Foo T K et al. Therapeutic targeting of BRCA1 and TP53 mutant breast cancer through mutant p53 reactivation. Npj Breast Cancer 2019; 5: 1-10.
44 Bertheau P, Lehmann-Che J, Varna M, Dumay A, Poirot B, Porcher R et al. p53 in breast cancer subtypes and new insights into response to chemotherapy. The Breast 2013; 22: S27-S29.
45 Greenblatt M S, Chappuis P O, Bond J P, Hamel N, Foulkes W D. TP53 Mutations in Breast Cancer Associated with BRCA1 or BRCA2 Germ-line Mutations: Distinctive Spectrum and Structural Distribution. Cancer Res 2001; 61: 4092-4097.
46 Jackson S P, Bartek J. The DNA-damage response in human biology and disease. Nature 2009; 461: 1071-1078.
47 Thapar R. Regulation of DNA Double-Strand Break Repair by Non-Coding RNAs. Mol Basel Switz 2018; 23. doi:10.3390/molecules23112789.
48 Syed A, Tainer J A. The MRE11-RAD50-NBS1 Complex Conducts the Orchestration of Damage Signaling and Outcomes to Stress in DNA Replication and Repair. Annu Rev Biochem 2018; 87: 263-294.
49 Harrow J, Frankish A, Gonzalez J M, Tapanari E, Diekhans M, Kokocinski F et al. GENCODE: the reference human genome annotation for The ENCODE Project. Genome Res 2012; 22: 1760-1774.

The invention claimed is:

1. A method of determining whether a subject has or is at a risk of developing a luminal breast cancer and treating the subject, comprising the steps of:

i) determining the expression level of the long intergenic non-coding RNA 01087 (LINC01087) in a tumor sample obtained from the subject, ii) comparing the expression level to a healthy tissue control and determining that the level in the tumor is higher than the control level, iii) determining that the tumor sample is or is likely a luminal breast cancer, and iii) treating the breast cancer with chemotherapy, radiation, immunotherapy and/or hormonotherapy.

2. The method according to claim 1 wherein the luminal breast cancer is Luminal A breast cancer or Luminal B breast cancer.

* * * * *